(12) United States Patent
Kim et al.

(10) Patent No.: US 9,385,325 B2
(45) Date of Patent: Jul. 5, 2016

(54) HETEROCYCLIC COMPOUND AND ORGANIC LIGHT EMITTING DEVICE INCLUDING THE SAME

(71) Applicant: SAMSUNG DISPLAY CO., LTD., Yongin, Gyeonggi-do (KR)

(72) Inventors: Young-Kook Kim, Yongin (KR); Seok-Hwan Hwang, Yongin (KR); Hye-Jin Jung, Yongin (KR); Jun-Ha Park, Yongin (KR); Eun-Young Lee, Yongin (KR); Jin-O Lim, Yongin (KR); Sang-Hyun Han, Yongin (KR); Eun-Jae Jeong, Yongin (KR); Soo-Yon Kim, Yongin (KR); Jong-Hyuk Lee, Yongin (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 208 days.

(21) Appl. No.: 13/827,371

(22) Filed: Mar. 14, 2013

(65) Prior Publication Data
US 2014/0124748 A1 May 8, 2014

(30) Foreign Application Priority Data

Nov. 5, 2012 (KR) .......................... 10-2012-0124468

(51) Int. Cl.
*H01L 51/50* (2006.01)
*H01L 51/00* (2006.01)
(Continued)

(52) U.S. Cl.
CPC .......... *H01L 51/0072* (2013.01); *C07D 209/56* (2013.01); *C07D 401/12* (2013.01);
(Continued)

(58) Field of Classification Search
None
See application file for complete search history.

(56) References Cited

U.S. PATENT DOCUMENTS 3,968,051 A 7/1976 Stamm et al.
4,521,605 A 6/1985 Okazaki et al.
(Continued)

FOREIGN PATENT DOCUMENTS

JP 1996-12600 A 1/1996
JP 11144873 A 5/1999
(Continued)

OTHER PUBLICATIONS

"A novel conjugated polymer based on 4H-benzo[def]carbazole backbone for OLED", 2009 Fall Assembly and Symposium, vol. 34, No. 2, 2009.

(Continued)

*Primary Examiner* — Gregory Clark
(74) *Attorney, Agent, or Firm* — Robert E. Bushnell, Esq.

(57) ABSTRACT

Provided is a heterocyclic compound represented by Formula 1 below and an organic light-emitting device including the compound of Formula 1:

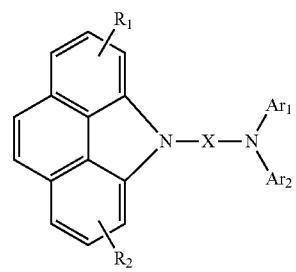

<Formula 1> wherein substituents in Formula 1 above are defined as in the specification.

20 Claims, 1 Drawing Sheet

(51) Int. Cl.
    *C07D 209/56*    (2006.01)
    *C07D 401/14*    (2006.01)
    *C07D 403/12*    (2006.01)
    *C07D 405/14*    (2006.01)
    *C07D 401/12*    (2006.01)
    *C07D 403/04*    (2006.01)
    *C07D 403/10*    (2006.01)
    *C07D 405/04*    (2006.01)
    *C07D 405/12*    (2006.01)
    *C07D 409/04*    (2006.01)
    *C07D 409/12*    (2006.01)
    *C07D 409/14*    (2006.01)

(52) U.S. Cl.
    CPC ............ *C07D401/14* (2013.01); *C07D 403/04* (2013.01); *C07D 403/10* (2013.01); *C07D 403/12* (2013.01); *C07D 405/04* (2013.01); *C07D 405/12* (2013.01); *C07D 405/14* (2013.01); *C07D 409/04* (2013.01); *C07D 409/12* (2013.01); *C07D 409/14* (2013.01); *H01L 51/0061* (2013.01); *H01L 51/0065* (2013.01)

(56) References Cited

U.S. PATENT DOCUMENTS

| | | | |
|---|---|---|---|
| 4,720,432 A | 1/1988 | VanSlyke et al. | |
| 5,061,569 A | 10/1991 | VanSlyke et al. | |
| 5,635,308 A | 6/1997 | Inoue et al. | |
| 5,972,247 A | 10/1999 | Shi et al. | |
| 6,242,115 B1 | 6/2001 | Thomson et al. | |
| 6,451,461 B2 | 9/2002 | Lee et al. | |
| 6,465,115 B2 | 10/2002 | Shi et al. | |
| 6,596,415 B2 | 7/2003 | Shi et al. | |
| 6,660,410 B2 | 12/2003 | Hosokawa | |
| 6,670,054 B1 | 12/2003 | Hu et al. | |
| 6,979,414 B2 | 12/2005 | Hosokawa | |
| 7,431,997 B2 | 10/2008 | Hwang et al. | |
| 2005/0221124 A1 | 10/2005 | Hwang et al. | |
| 2008/0258615 A1* | 10/2008 | Begley et al. | 313/504 |
| 2009/0302752 A1* | 12/2009 | Parham et al. | 313/504 |
| 2012/0292603 A1* | 11/2012 | Kwak et al. | 257/40 |
| 2013/0168646 A1* | 7/2013 | Kim | 257/40 |

FOREIGN PATENT DOCUMENTS

| | | |
|---|---|---|
| JP | 2000-003782 A | 1/2000 |
| JP | 2000302756 A | 10/2000 |
| JP | 2003133075 A | 5/2003 |
| JP | 2004079265 A | 3/2004 |
| JP | 2006151979 A | 6/2006 |
| KR | 10-0346984 B1 | 7/2002 |
| KR | 100573137 B1 | 4/2006 |

OTHER PUBLICATIONS

U.S. Appl. No. 13/826,319, filed Mar. 14, 2013.
Sigma-Aldrich, 4H-benzordeficarbazole, printed on Sep. 2, 2015 from www.sigmaaldrich.com.

* cited by examiner

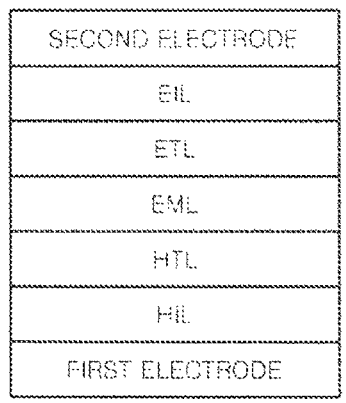

HETEROCYCLIC COMPOUND AND ORGANIC LIGHT EMITTING DEVICE INCLUDING THE SAME

CLAIM OF PRIORITY

This application makes reference to, incorporates the same herein, and claims all benefits accruing under 35 U.S.C. §119 from an application for HETEROCYCLIC COMPOUND AND ORGANIC LIGHT EMITTING DEVICE INCLUDING THE SAME earlier filed in the Korean Intellectual Property Office on 5 Nov. 2012 and there duly assigned Serial No. 10-2012-0124468.

BACKGROUND OF THE INVENTION

1. Field of the Invention

The present invention relates to a heterocyclic compound and an organic light-emitting device including the same.

2. Description of the Related Art

Organic light-emitting devices (OLEDs), which are self-emitting devices, have advantages such as wide viewing angles, excellent contrast, quick response, high brightness, excellent driving voltage characteristics, and can provide multicolored images.

A typical OLED has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

There is an ongoing demand for a material having improved electrical stability, high charge-transfer or emission capability, a high glass transition temperature, and capable of preventing crystallization, relative to existing unimolecular materials.

SUMMARY OF THE INVENTION

The present invention provides a novel compound with improved characteristics, and a high-efficiency, low-voltage, high-luminance, and long-lifetime organic light-emitting device including the novel compound. The novel compound has improved electrical characteristics, good charge transporting capabilities, improved emission capability, a high glass transition temperature (Tg) enough to prevent crystallization. The novel compound is suitable as a hole transporting or injecting material for fluorescent or phosphorescent device of any color, or as a red green, blue, or white light-emitting material.

According to an aspect of the present invention, there is provided there is provided a heterocyclic compound represented by Formula 1 below:

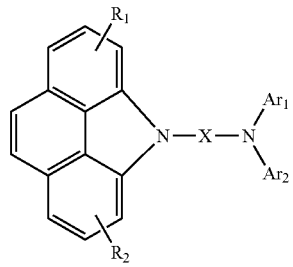

<Formula 1> wherein, in Formula 1, $R_1$ and $R_2$ may be each independently a hydrogen atom, a deuterium atom, a halogen atom, a cyano group, a nitro group, a C1-C60 alkylsilyl group, a C1-C60 arylsilyl group, a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C6-C60 aryl group, a substituted or unsubstituted C3-C60 heteroaryl group, a substituted or unsubstituted C6-C60 aryloxy group, or a substituted or unsubstituted C6-C60 arylthio group; X is a divalent linking group of a substituted or unsubstituted C6-C60 arylene group, a substituted or unsubstituted C3-C60 heteroarylene group, or a substituted or unsubstituted C6-C60 condensed polycyclic group; and $Ar_1$ and $Ar_2$ may be each independently a substituted or unsubstituted C6-C60 aryl group, a substituted or unsubstituted C3-C60 heteroaryl group, or a substituted or unsubstituted C6-C60 condensed polycyclic group.

According to another aspect of the present invention, there is provided an organic light-emitting device including a first electrode, a second electrode, and an organic layer disposed between the first electrode and the second electrode, wherein the organic layer includes the compound of Formula 1 described above.

According to another aspect of the present invention, there is provided a flat panel display device including the above-described organic light-emitting device, wherein the first electrode of the organic light-emitting device is electrically connected to a source electrode or a drain electrode of a thin-film transistor.

BRIEF DESCRIPTION OF THE DRAWINGS

The above and other features and advantages of the present invention will become more apparent by describing in detail exemplary embodiments thereof with reference to the attached drawings in which:

FIG. 1 is a schematic view of a structure of an organic light-emitting device according to an embodiment of the present invention.

DETAILED DESCRIPTION OF THE INVENTION

As used herein, the term "and/or" includes any and all combinations of one or more of the associated listed items. Expressions such as "at least one of," when preceding a list of elements, modify the entire list of elements and do not modify the individual elements of the list.

According to an aspect of the present invention, there is provided a compound represented by Formula 1 below.

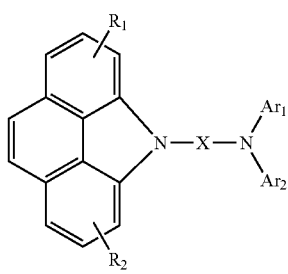

<Formula 1>

In Formula 1, $R_1$ and $R_2$ may be each independently a hydrogen atom, a deuterium atom, a halogen atom, a cyano group, a nitro group, a C1-C60 alkylsilyl group, a C1-C60 arylsilyl group, a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C6-C60 aryl group, a substituted or unsubstituted C3-C60 heteroaryl group, a substituted or unsubstituted C6-C60 aryloxy group, or a substituted or unsubstituted C6-C60 arylthio group; X is a divalent linking group of a substituted or unsubstituted C6-C60 arylene group, a substituted or unsubstituted C3-C60 heteroarylene group, or a substituted or unsubstituted C6-C60 condensed polycyclic group; and $Ar_1$ and $Ar_2$ may be each independently a substituted or unsubstituted C6-C60 aryl group, a substituted or unsubstituted C3-C60 heteroaryl group, or a substituted or unsubstituted C6-C60 condensed polycyclic group.

The compound of Formula 1 above may serve as a hole injecting material or a hole transporting material for organic light-emitting devices. The compound of Formula 1 has a high glass transition temperature (Tg) or a high melting point due to the inclusion of the heterocyclic ring. Thus, the compound of Formula 1 may have improved heat resistance against Joule's heat generated between organic layers or between an organic layer and a metal electrode when light emission occurs and have high durability in high-temperature environments. An organic light-emitting device manufactured using the heterocyclic compound of Formula 1 may have improved durability when stored or operated.

Substituents in the compound of Formula 1 will now be described in detail.

In some embodiments, in Formula 1, $Ar_1$ and $Ar_2$ may be linked to form a ring.

In some embodiments, in Formula 1, $R_1$ and $R_2$ may be one of the groups represented by a hydrogen atom, a deuterium atom, CN, F, $CF_3$, $Si(R_{40})_3$, or

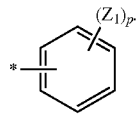

$Z_1$ may be a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen group, a cyano group, a nitro group, a hydroxy group, or a carboxy group; $R_{40}$ may be a substituted or unsubstituted C1-C20 alkyl group, a substituted or unsubstituted C5-C20 aryl group, a substituted or unsubstituted C3-C20 heteroaryl group, or a substituted or unsubstituted C6-C20 condensed polycyclic group; p is an integer from 1 to 5; and * indicates a binding site.

In some emodiments, in Formula 1, X may be one of the groups represented by Formulae 2a to 2g.

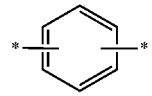
2a

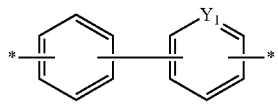
2b

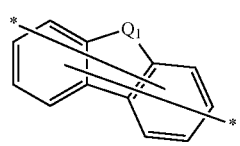
2c

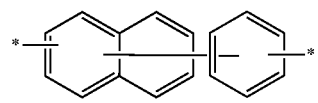
2d

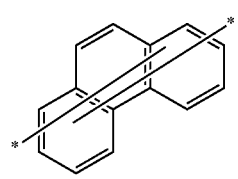
2e

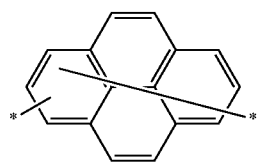
2f

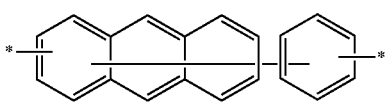
2g

In Formulae 2a to 2g, $Q_1$ may be a linking group represented by —$C(R_{30})(R_{31})$—, —S—, —O—, or —$NR_{32}$—; $Y_1$ may be CH or N; $R_{30}$, $R_{31}$, and $R_3$ may be each independently, a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen group, a cyano group, a nitro group, a hydroxy group, or a carboxy group; and * indicates a binding site.

In some other embodiments, in Formula 1, $Ar_1$ and $Ar_2$ may be each independently one of the group represented by Formulae 3a to 3e below.

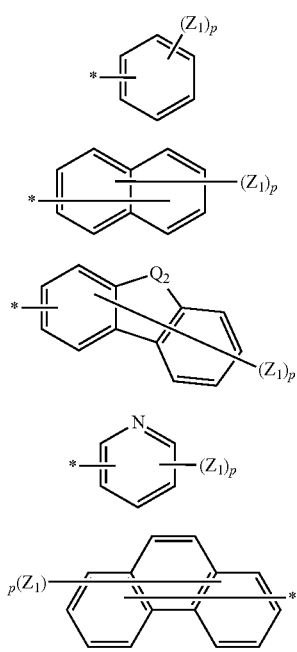

In Formulae 3a to 3e, $Q_2$ may be a linking group represented by —C($R_{30}$)($R_{31}$)—, —N($R_{32}$)—, —S—, or —O—; $Z_1$, $R_{30}$, $R_{31}$, and $R_{32}$ may be each independently, a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, —Si($R_{40}$)$_3$, a halogen group, a cyano group, a nitro group, a hydroxy group or a carboxy group; $R_{40}$ may be a substituted or unsubstituted C1-C20 alkyl group, a substituted or unsubstituted C5-C20 aryl group, a substituted or unsubstituted C3-C20 heteroaryl group, or a substituted or unsubstituted C6-C20 condensed polycyclic group; p is an integer from 1 to 9; and * indicates a binding site.

In Formula 3c, when $Q_2$ is represented by —C($R_{30}$)($R_{31}$)—, optionally, $R_{30}$ and $R_{31}$ may be linked to each other and form a ring.

Hereinafter, substituents described with reference to the formulae will now be described in detail. In this regard, the numbers of carbons in substituents are presented only for illustrative purposes and do not limit the characteristics of the substituents.

The unsubstituted C1-C60 alkyl group may be linear or branched. Non-limiting examples of the unsubstituted C1-C60 alkyl group are methyl, ethyl, propyl, isobutyl, sec-butyl, pentyl, iso-amyl, hexyl, heptyl, octyl, nonanyl, and dodecyl. At least one hydrogen atom of the unsubstituted C1-C60 alkyl group may be substituted with a deuterium atom, a halogen atom, a hydroxy group, a nitro group, a cyano group, an amino group, an amidino group, a hydroxyrazine, a hydroxyrazone, a carboxyl group or a salt thereof, a sulfonic acid group or a salt thereof, a phosphoric acid group or a salt thereof, or a C1 to 10 alkyl group, a C1 to 10 alkoxy group, a C2 to 10 alkenyl group, a C2 to 10 alkynyl group, a C6 to 16 aryl group, or a C4 to 16 heteroaryl group.

The unsubstituted C2-C60 alkenyl group indicates an unsaturated alkyl groups having at least one carbon-carbon double bond in the center or at a terminal of the alkyl group. Examples of the alkenyl group are an ethenyl group, a propenyl group, a butenyl group, and the like. At least one hydrogen atom in the unsubstituted alkenyl group may be substituted with a substituent described above in conjunction with the alkyl group.

The unsubstituted C2-C60 alkynyl group indicates an alkyl group having at least one carbon-carbon triple bond in the center or at a terminal of the alkyl group. Non-limiting examples of the unsubstituted C2-C20 alkynyl group are acetylene, propylene, phenylacetylene, naphthylacetylene, isopropylacetylene, t-butylacetylene, and diphenylacetylene. At least one hydrogen atom in the alkynyl group may be substituted with a substituent described above in conjunction with the alkyl group.

The unsubstituted C3-C60 cycloalkyl group indicates a C3-C60 cyclic alkyl group wherein at least one hydrogen atom in the cycloalkyl group may be substituted with a substituent described above in conduction with the C1-C60 alkyl group.

The unsubstituted C1-C60 alkoxy group indicates a group having a structure of —OA wherein A is an unsubstituted C1-C60 alkyl group as described above. Non-limiting examples of the unsubstituted C1-C60 alkoxy group are a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted C6-C60 aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with a substituent described above in conjunction with the unsubstituted C1-C60 alkyl group.

Non-limiting examples of the a substituted or unsubstituted C5-C60 aryl group are a phenyl group, a C1-C10 alkylphenyl group (for example, ethylphenyl group), a halophenyl group (for example, o-, m-, and p-fluorophenyl group, dichlorophenyl group), a cyanophenyl group, dicyanophenyl group, a trifluoromethoxyphenyl group, a biphenyl group, a halobiphenyl group, a cyanobiphenyl group, a C1-C10 alkyl biphenyl group, a C1-C10 alkoxybiphenyl group, a o-, m-, and p-toryl group, an o-, m-, and p-cumenyl group, a mesityl group, a phenoxyphenyl group, a (α,α-dimethylbenzene) phenyl group, a (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a C1-C10 alkylnaphthyl group (for example, methylnaphthyl group), a C1-C10 alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted C3-C60 heteroaryl group used herein includes one, two or three hetero atoms selected from N, O, P and S. At least two rings may be fused to each other or linked to each other by a single bond. Non-limiting examples of the unsubstituted C4-C60 heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent described above in conjunction with the unsubstituted C1-C60 alkyl group.

The unsubstituted C6-C60 aryloxy group is a group represented by —OA$_1$ wherein A$_1$ may be a C6-C60 aryl group. An example of the aryloxy group is a phenoxy group. At least one hydrogen atom in the aryloxy group may be substituted with a substituent described above in conjunction with the unsubstituted C1-C60 alkyl group.

The unsubstituted C6-C60 arylthio group is a group represented by —SA$_1$ wherein A$_1$ may be a C6-C60 aryl group. Non-limiting examples of the arylthio group are a benzenethio group and a naphthylthio group. At least one hydrogen atom in the arylthio group may be substituted with a substituent described above in conjunction with the unsubstituted C1-C60 alkyl group.

The unsubstituted C6-C60 condensed polycyclic group used herein refers to a substituent including at least two rings wherein at least one aromatic ring and/or at least one non-aromatic ring are fused to each other, or refers to a substituent having an unsaturated group in a ring that may not form a conjugate structure. The unsubstituted C6-C60 condensed polycyclic group is distinct from an aryl group or a heteroaryl group in terms of being non-aromatic.

Non-limiting examples of the compound represented by Formula 1 are compounds represented by the following formulae.

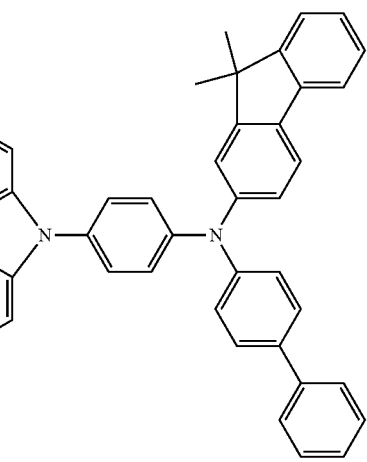
1

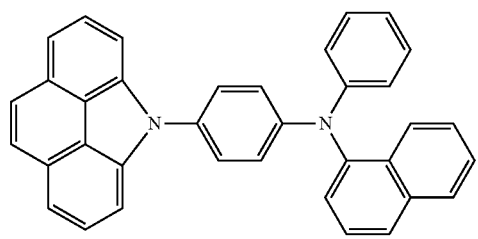
2

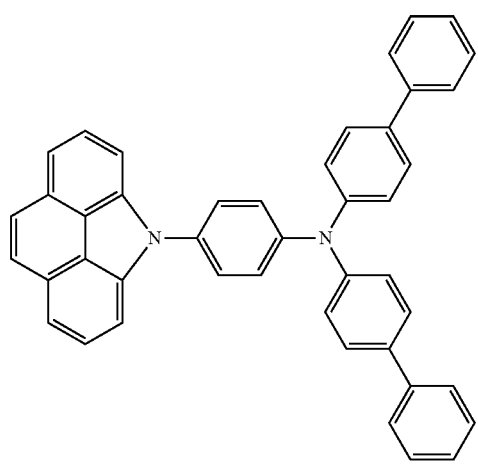

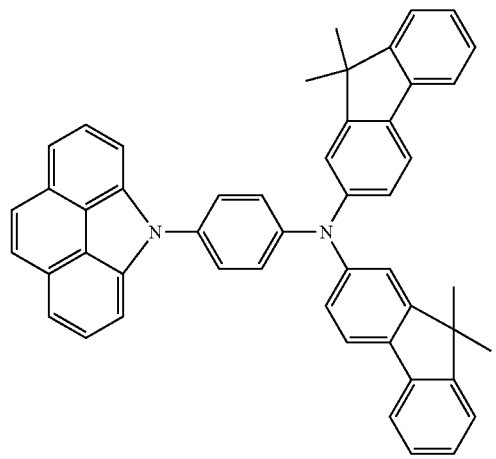
3

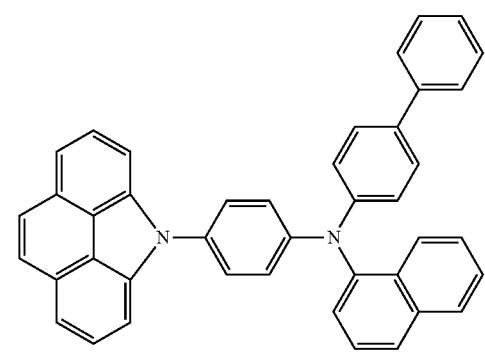
4

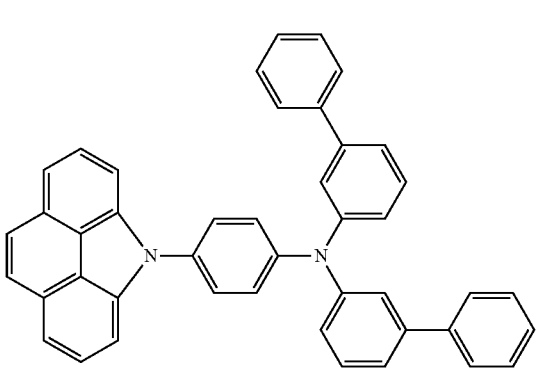
5

6

-continued
7
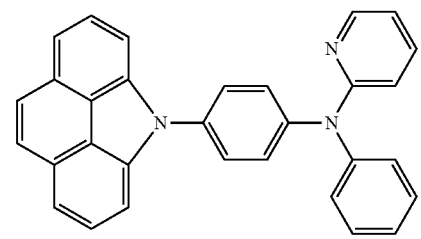
8
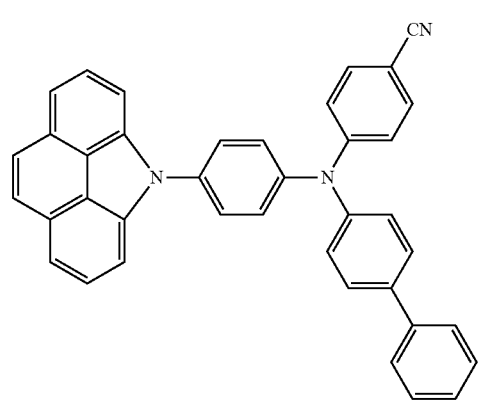
9
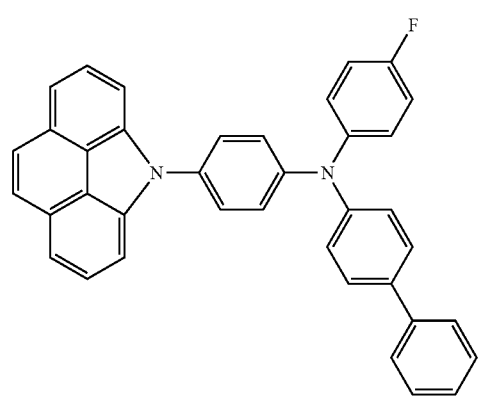
10
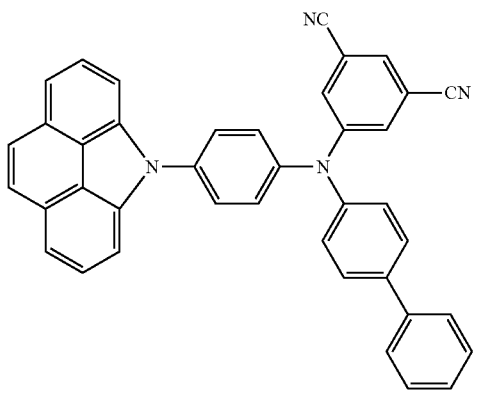
-continued
11
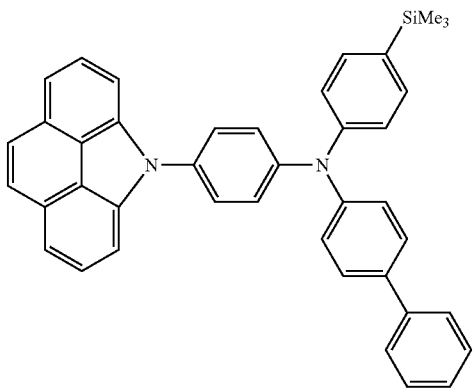
12
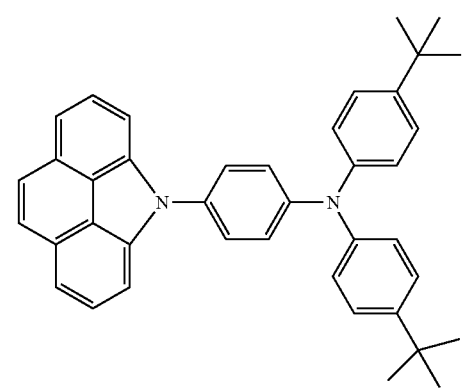
13
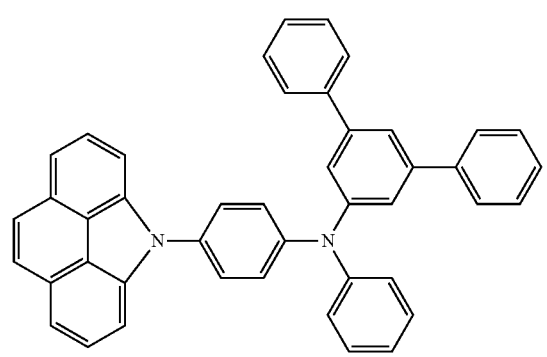
14
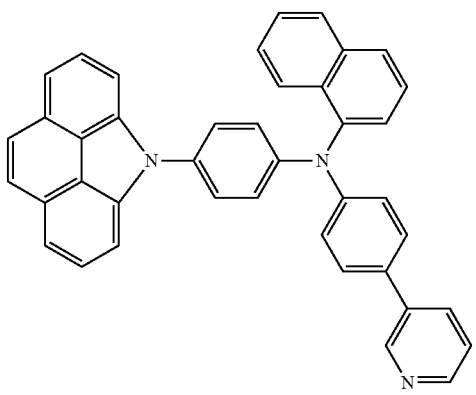

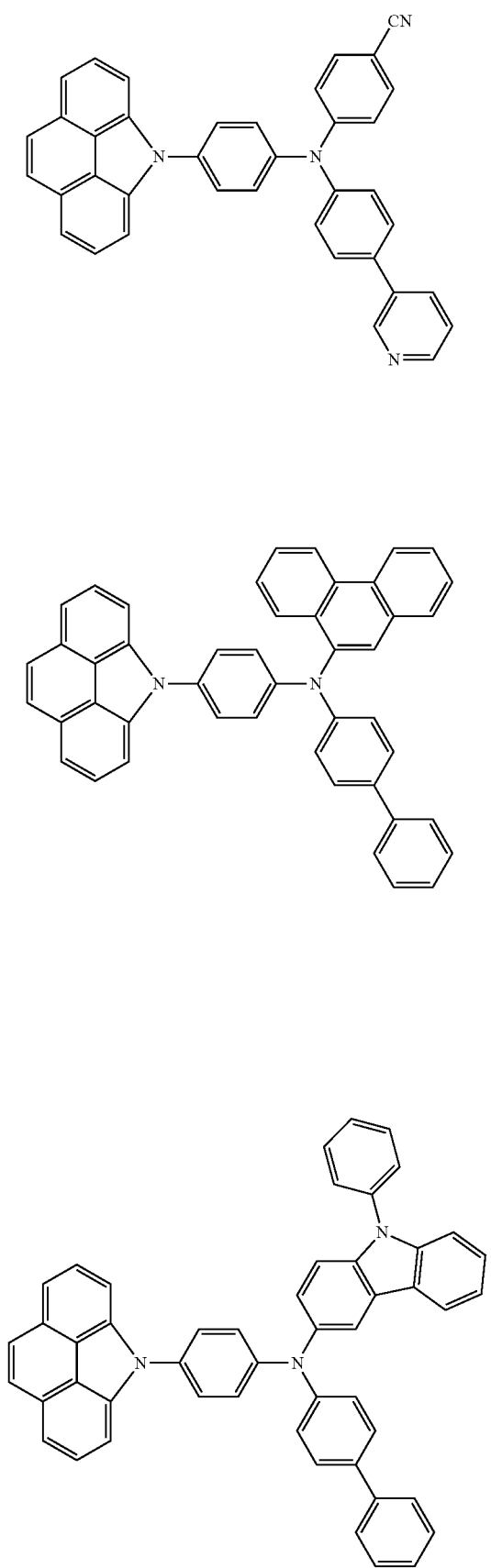

-continued
22
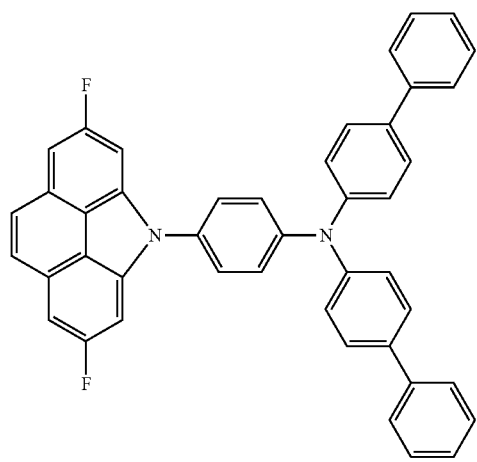
23
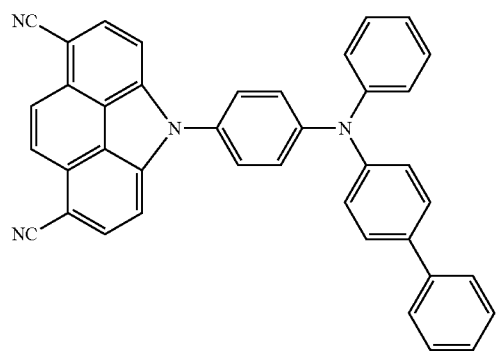
24
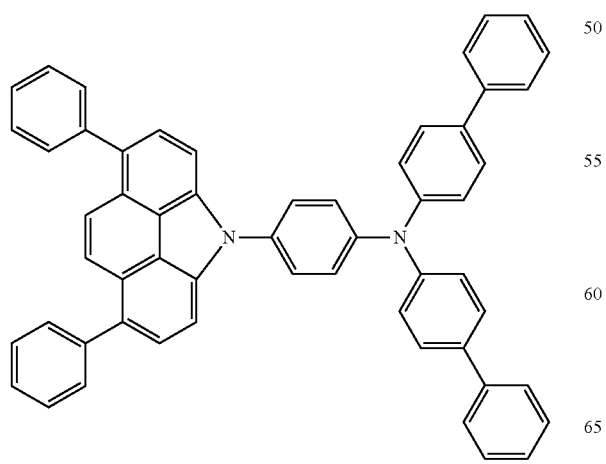
-continued
25
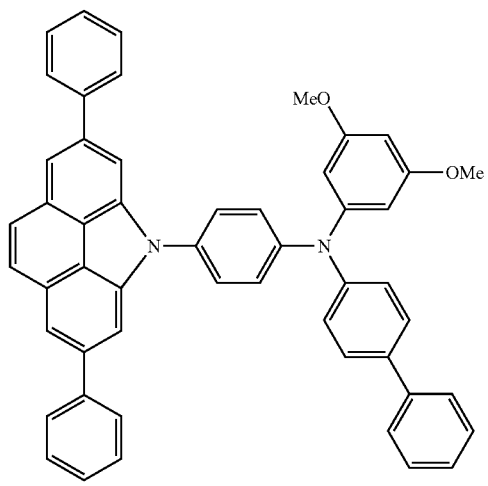
26
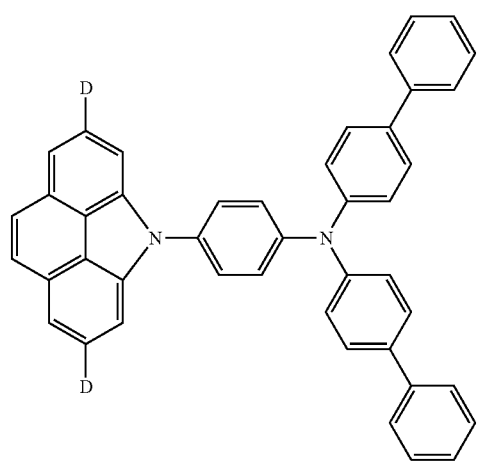
27
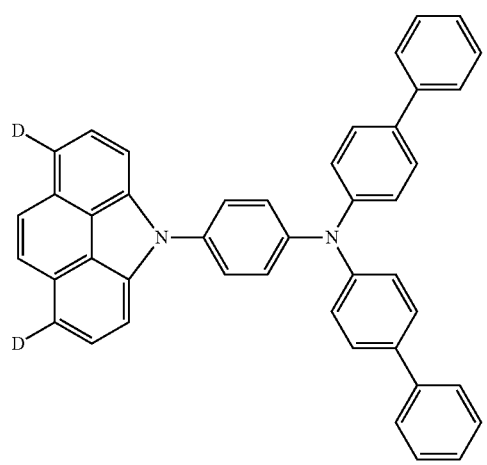

28
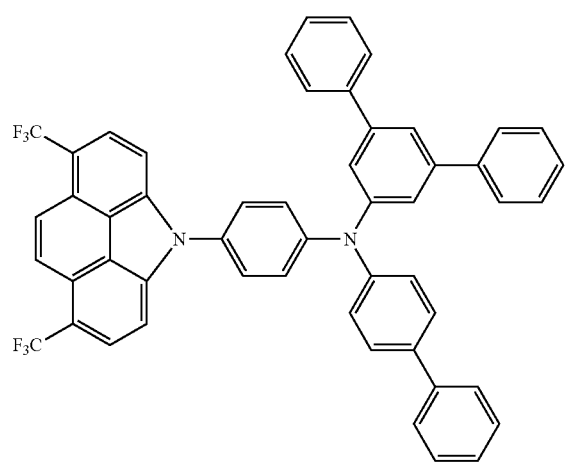
29
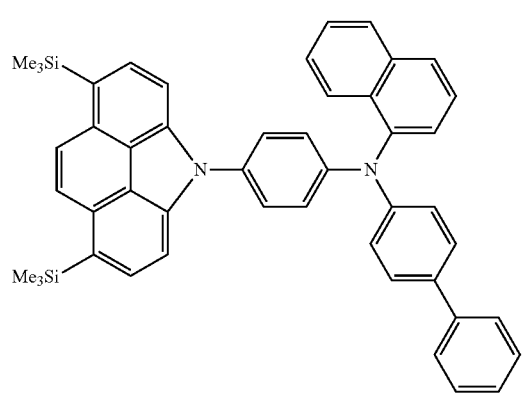
30
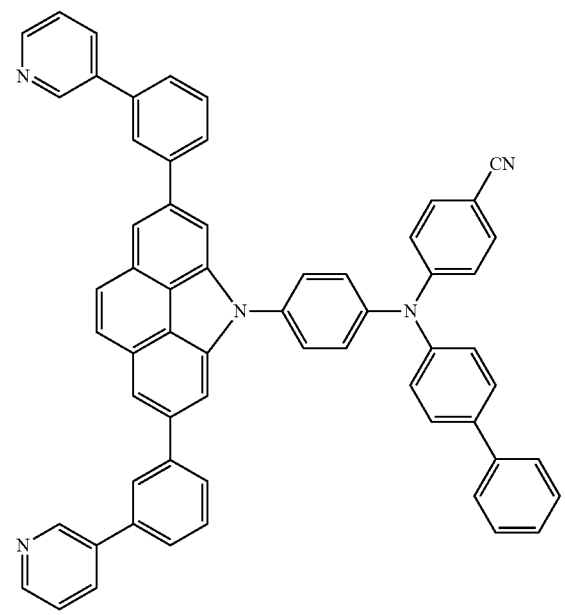
31
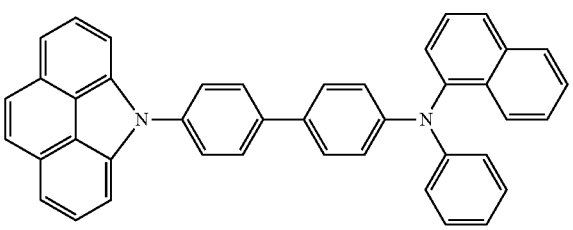
32
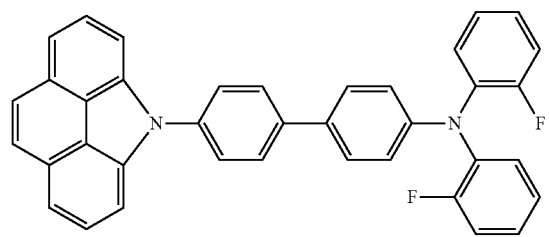
33
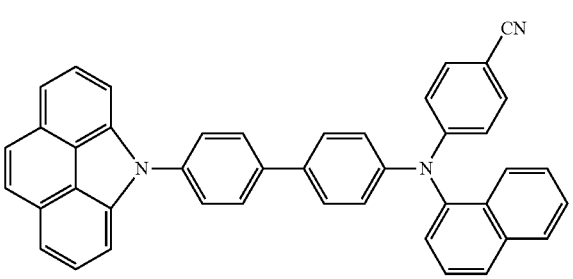
34
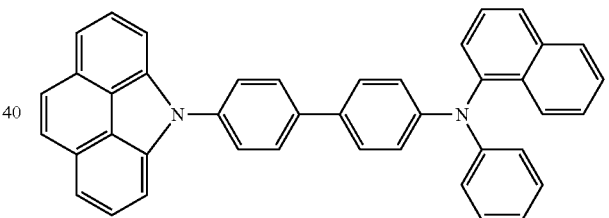
35
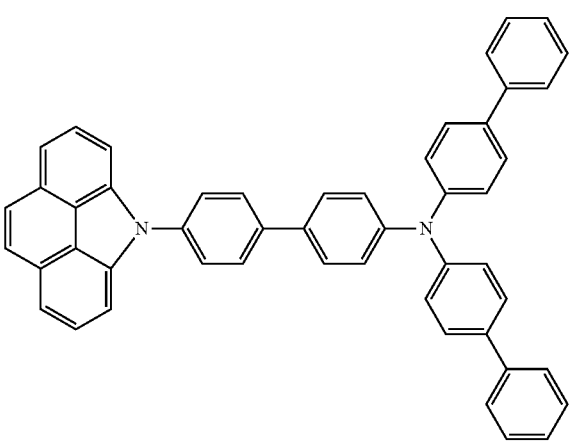

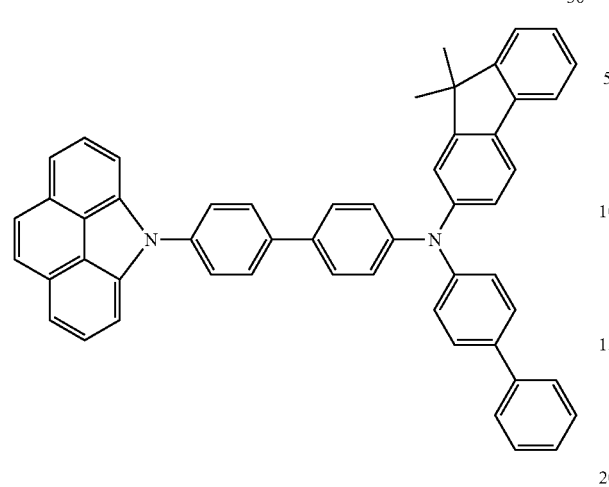
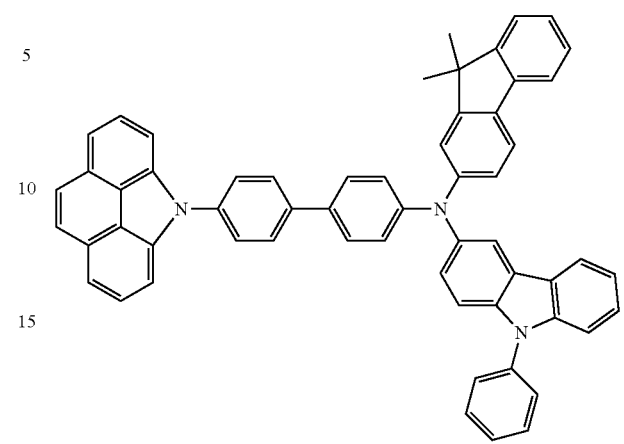
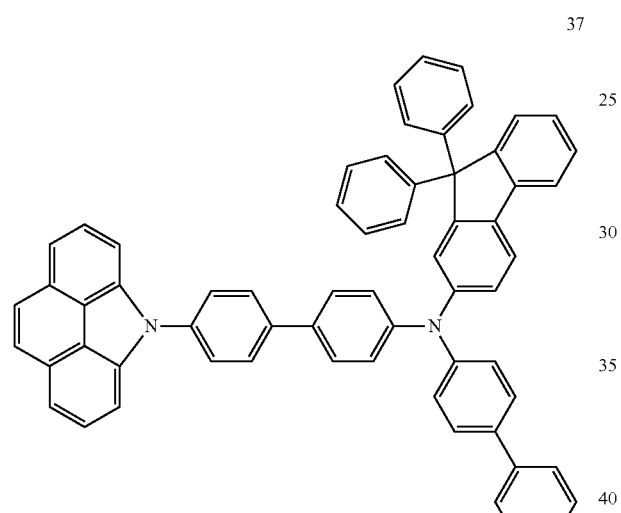
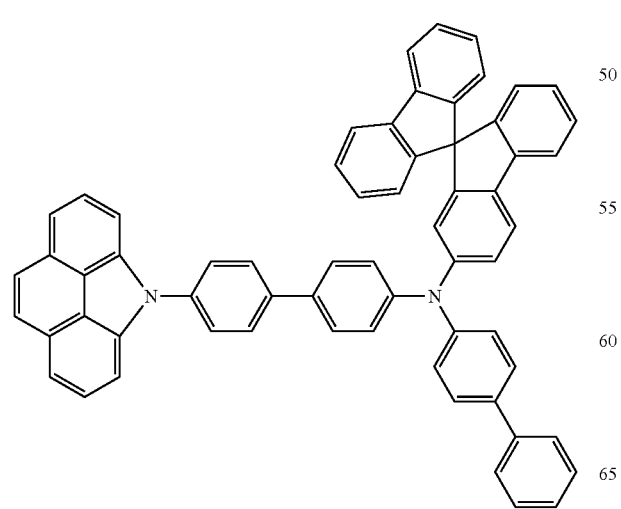

43
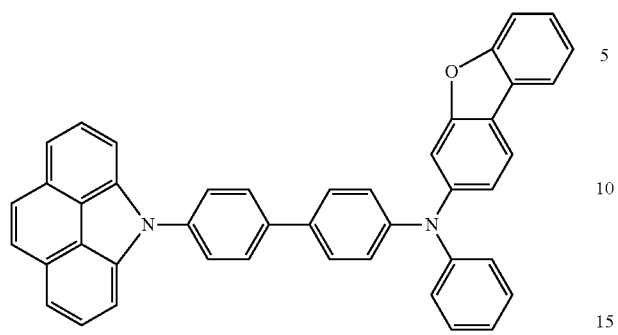
44
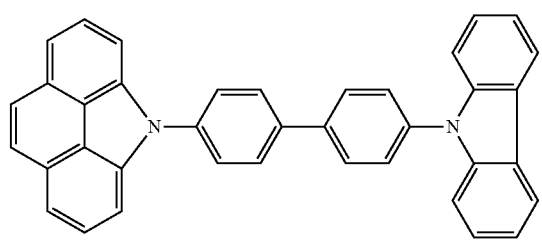
45
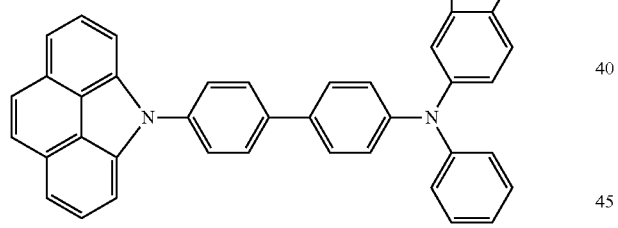
46
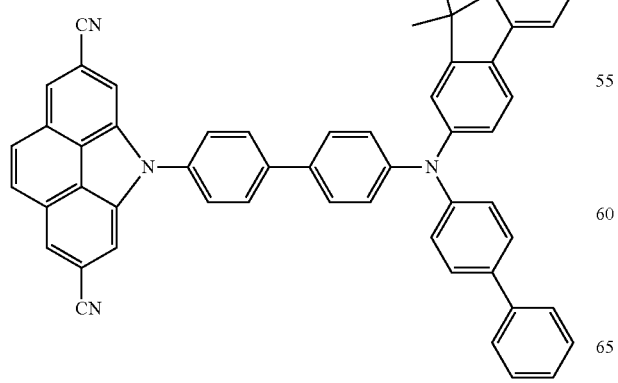
47
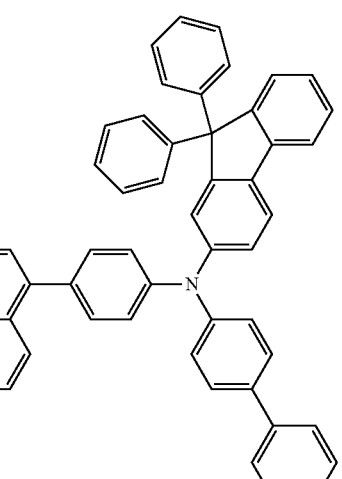
48
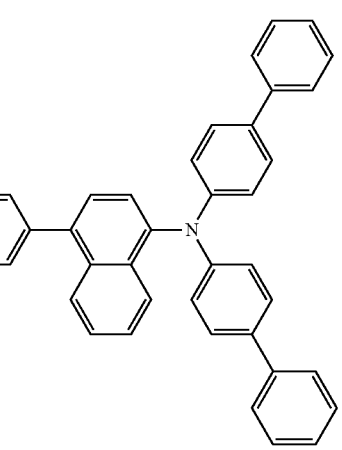
49
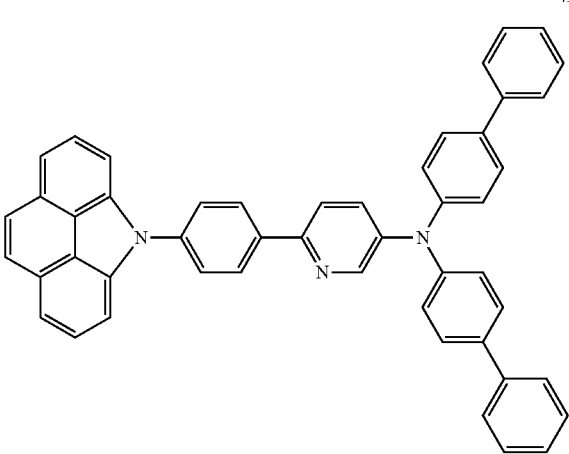

US 9,385,325 B2
-continued
50
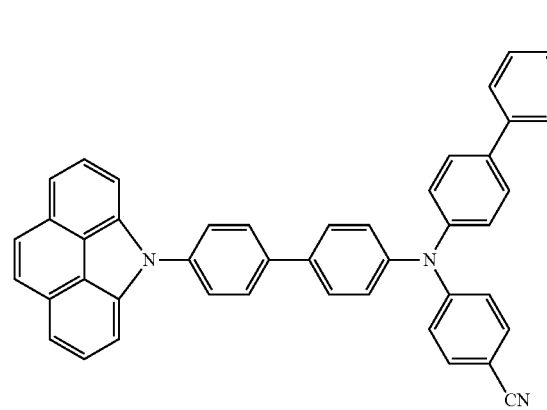
51
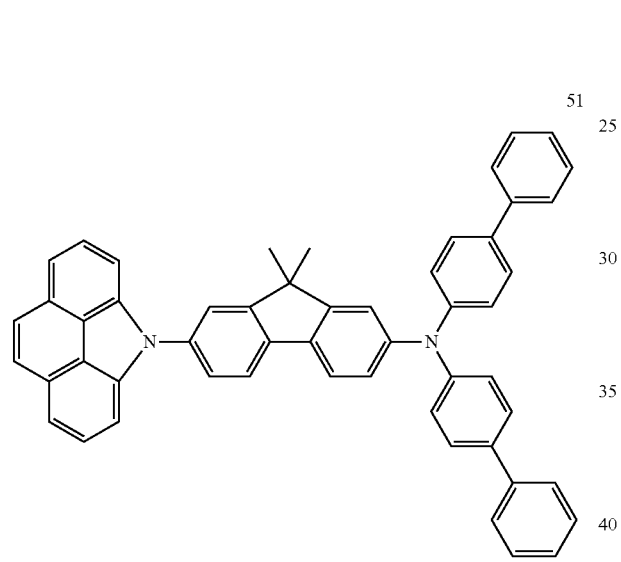
52
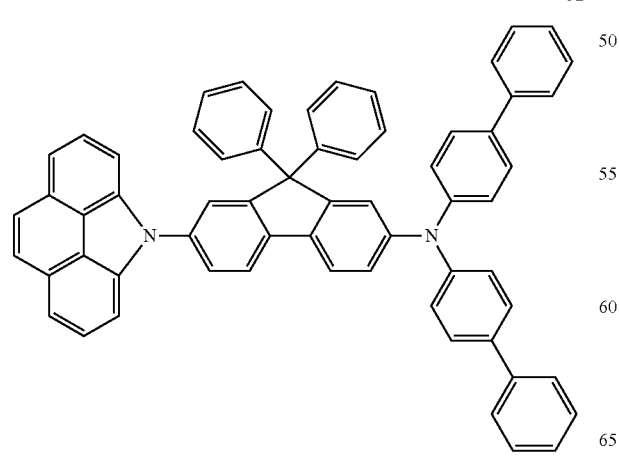
-continued
53
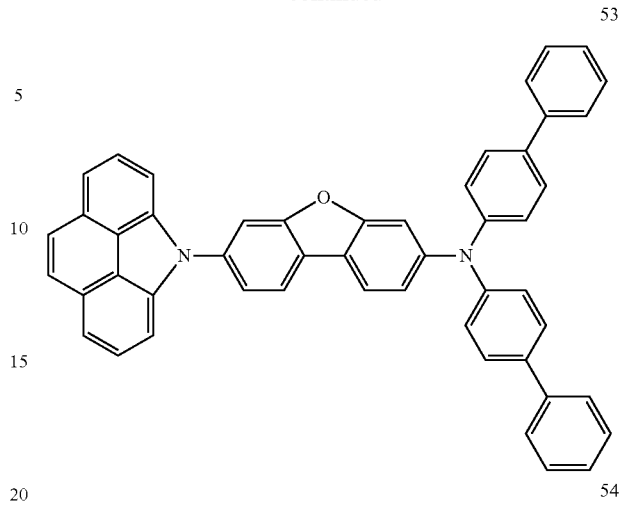
54
55
56
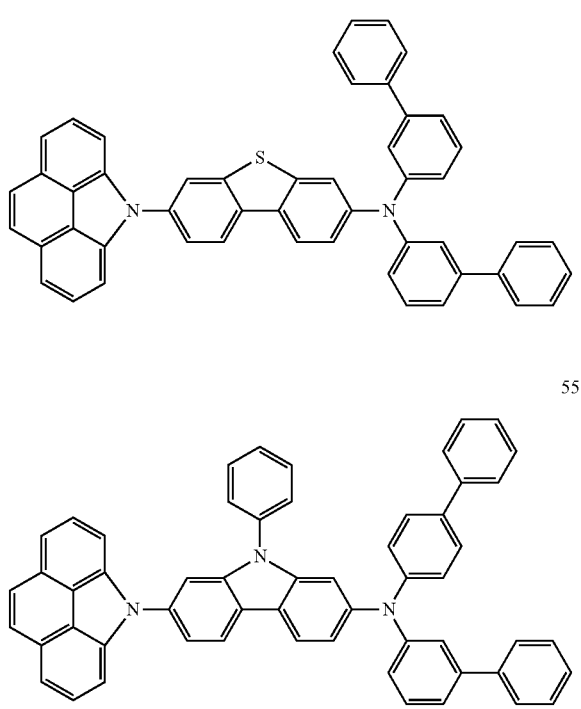
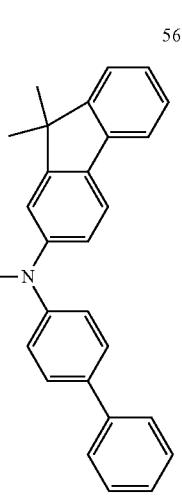

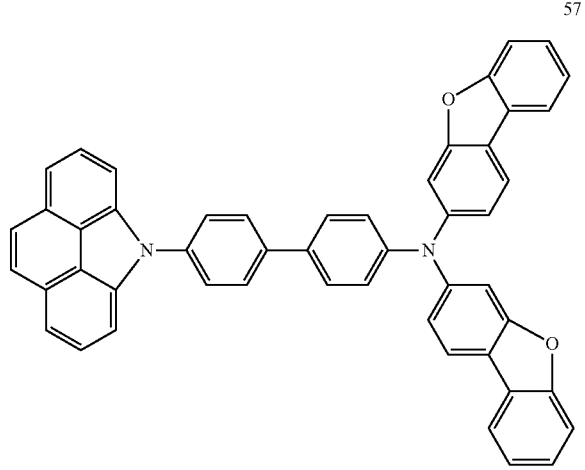

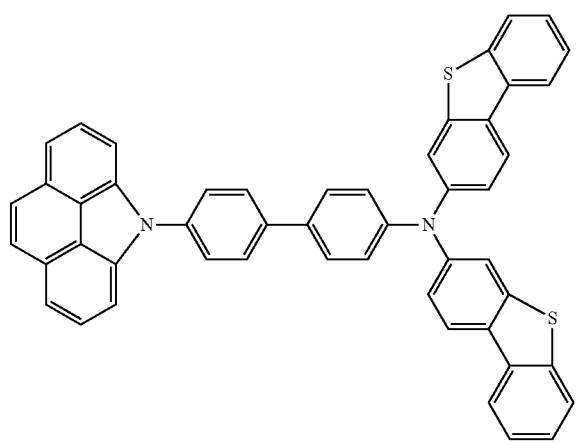

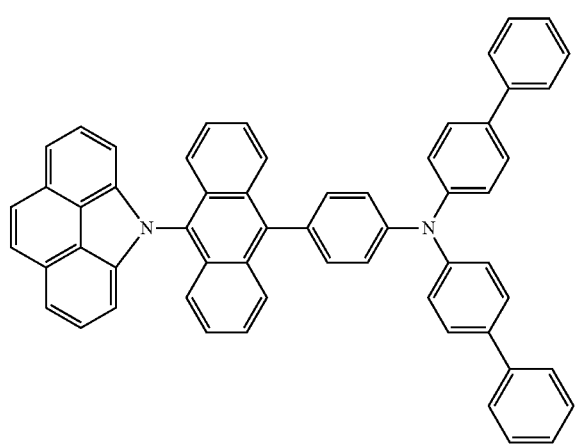

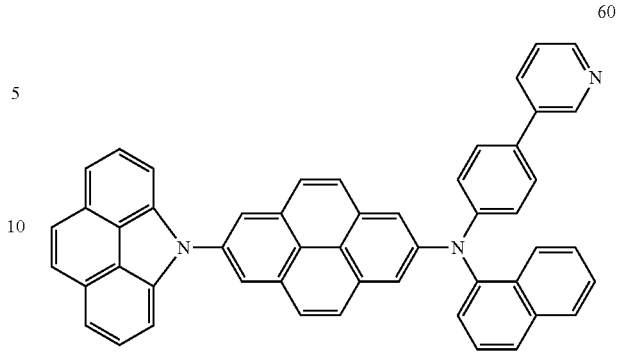

Another aspect of the present invention provides an organic light-emitting device including a first electrode, a second electrode, and an organic layer disposed between the first electrode and the second electrode, wherein the organic layer includes the compound of Formula 1 described above.

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

In particular, the organic layer may be used as a hole injection layer, a hole transport layer, or a functional layer having both hole injection and transport capabilities. The hole transport layer may include multiple layers, and the functional layer may also include multiple layers. For example, the hole transport layer may include two layers. One of the two layers of the hole transport layer that is in contact with the hole injection layer may include a known hole transport material, and one of the two layers of the hole transport layer that is in contact with the emission layer may include the compound of Formula 1.

In some embodiments, the organic light-emitting device may include an electron injection layer, an electron transport layer, an emission layer, a hole injection layer, a hole transport layer, or a functional layer having both hole injection and transport capabilities; the hole injection layer, the hole transport layer, or the functional layer having both hole injection and transport capabilities may include the compound of Formula 1 above; and the emission layer may include an anthracene-based compound, an arylamine-based compound or a styryl-based compound.

In some other embodiments, the organic light-emitting device may include an electron injection layer, an electron transport layer, an emission layer, a hole injection layer, a hole transport layer, or a functional layer having both hole injection and transport capabilities; at least one of a red emission layer, a green emission layer, a blue emission layer, and a white emission layer of the emission layer may include a phosphorescent compound; and at least one of the hole injection layer, the hole transport layer, and the functional layer having both hole injection and hole transport capabilities may further include a charge-generating material, in addition to the compound of the present invention. In some embodiments, the charge-generating material may be a p-dopant, and the p-dopant may be a quinine derivative, a metal oxide, or a cyano group-containing compound.

In some embodiments, the organic layer may include an electron transport layer, and the electron transport layer may include an electron-transporting organic compound and a metal complex. The metal complex may be a lithium (Li) complex.

The term "organic layer" as used herein refers to a single layer and/or a plurality of layers disposed between the first and second electrodes of the organic light-emitting device.

The organic layer may include an emission layer, and the emission layer may include the compound of Formula 1 described above. The organic layer may include at least one of a hole injection layer, a hole transport layer, and a functional layer having both hole injection and hole transport capabilities (hereinafter, "H-functional layer"); and at least one of the hole injection layer, the hole transport layer, and the functional layer having both hole injection and hole transport capabilities may include the compound of Formula 1.

FIG. 1 is a schematic sectional view of an organic light-emitting device according to an embodiment of the present invention. Hereinafter, a structure of an organic light-emitting device according to an embodiment of the present invention and a method of manufacturing the same will now be described with reference to FIG. 1.

A substrate (not shown) may be any substrate that is used in existing organic light emitting devices. In some embodiments the substrate may be a glass substrate or a transparent plastic substrate with strong mechanical strength, thermal stability, transparency, surface smoothness, ease of handling, and water resistance.

The first electrode may be formed by depositing or sputtering a first electrode-forming material on the substrate. When the first electrode is an anode, a material having a high work function may be used as the first electrode-forming material to facilitate hole injection. The first electrode may be a reflective electrode or a transmission electrode. Transparent and conductive materials such as ITO, IZO, $SnO_2$, and ZnO may be used to form the first electrode. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode may have a single-layer structure or a multi-layer structure including at least two layers. For example, the first electrode may have a three-layered structure of ITO/Ag/ITO, but is not limited thereto.

An organic layer may be disposed on the first electrode.

The organic layer may include a hole injection layer (HIL), a hole transport layer (HTL), a buffer layer (not shown), an emission layer (EML), an electron transport layer (ETL), or an electron injection layer (EIL).

The HIL may be formed on the first electrode by vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ ton, and a deposition rate of about 0.01 to about 100 Å/sec. However, the deposition conditions are not limited thereto.

When the HIL is formed using spin coating, the coating conditions may vary according to the material that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

The HIL may be formed of any material that is commonly used to form a HIL, in addition to the compound of Formula 1. Non-limiting examples of the material that can be used to form the HIL are N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4"-tris (3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrene sulfon ate) (PEDOT/PSS), polyaniline/camphor sulfonicacid (Pani/CSA), and polyaniline)/poly(4-styrenesulfonate (PANI/PSS).

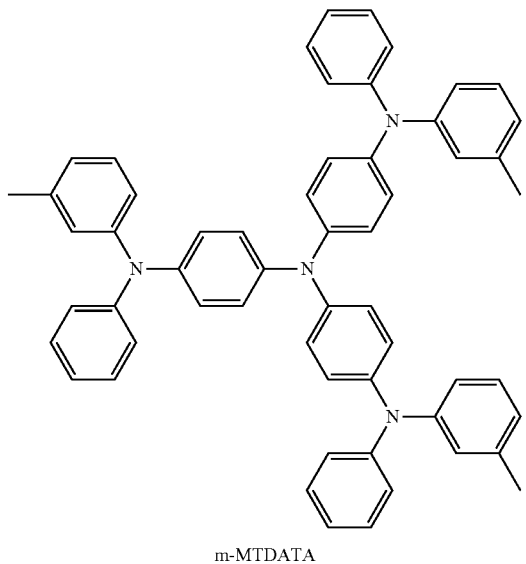

m-MTDATA

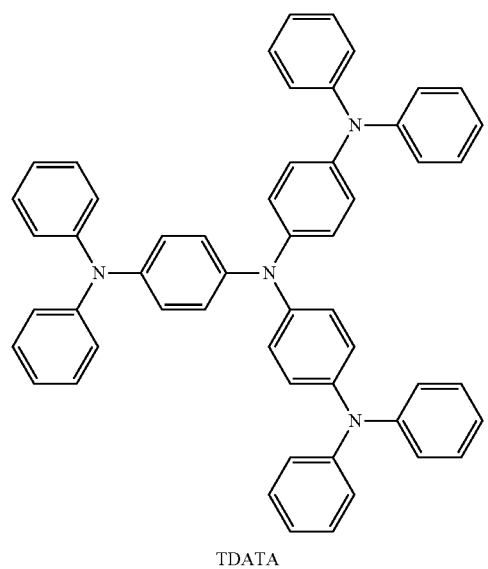

TDATA

-continued

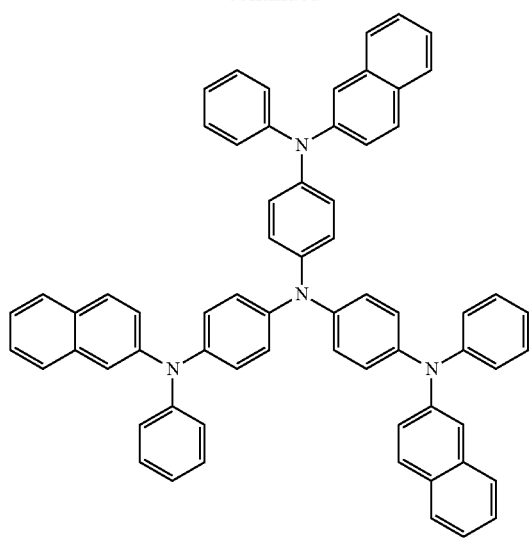

2-TNATA

The thickness of the HIL may be from about 100 Å to about 10000 Å, and in some embodiments, may be from about 100 Å to about 1000 Å. When the thickness of the HIL is within these ranges, the HIL may have good hole injecting ability without a substantial increase in driving voltage.

Then, a HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to the material that is used to form the HTL.

The HTL may be formed of the compound of Formula 1 or any known hole transporting materials. Non-limiting examples of suitable known HTL forming materials are carbazole derivatives, such as N-phenylcarbazole or polyvinylcarbazole, N,N'-bis(3-methylphenyl)-N,N-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB).

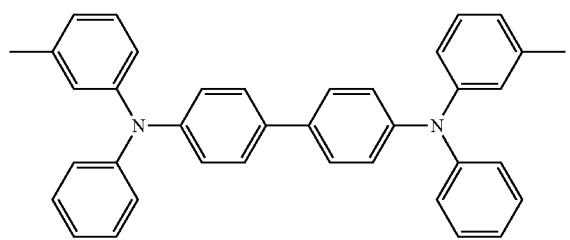

TPD

-continued

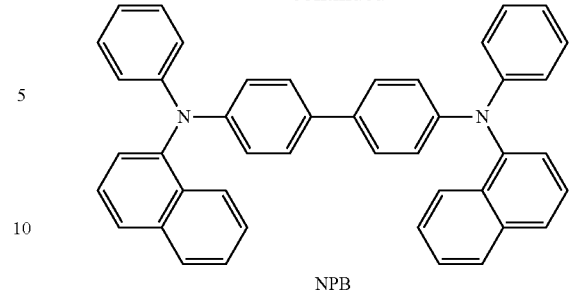

NPB

The thickness of the HTL may be from about 50 Å to about 2000 Å, and in some embodiments, from about 100 Å to about 1500 Å. When the thickness of the HTL is within these ranges, the HTL may have good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 500 Å to about 10,000 Å, and in some embodiments, may be from about 100 Å to about 1,000 Å. When the thickness of the H-functional layer is within these ranges, the H-functional layer may have good hole injection and transport capabilities without a substantial increase in driving voltage.

In some embodiments, at least one of the HIL, HTL, and H-functional layer may include at least one of a compound of Formula 300 below and a compound of Formula 350 below:

<Formula 300>

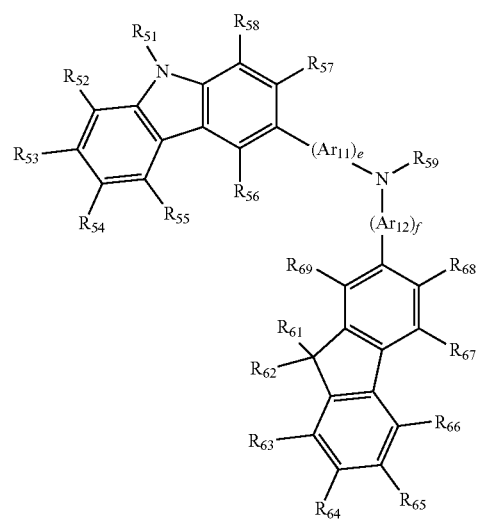

<Formula 350>

In Formulae 300 and 350, $Ar_{17}$, $Ar_{12}$, $Ar_{21}$, and $Ar_{22}$ may be each independently a substituted or unsubstituted $C_5$-$C_{60}$ arylene group.

In Formula 300, e and f may be each independently an integer from 0 to 5, for example, may be 0, 1, or 2. In a non-limiting embodiment, e may be 1, and f may be 0.

In Formulae 300 and 350 above, $R_{51}$ to $R_{58}$, $R_{61}$ to $R_{69}$, and $R_{71}$ to $R_{72}$ may be each independently a hydrogen atom, a deuterium atom, a halogen atom, a hydroxyl group, a cyano group, a nitro group, an amino group, an amidino group, a hydrazine group, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. In some embodiments, $R_{51}$ to $R_{58}$, $R_{61}$ to $R_{69}$, $R_{71}$, and $R_{72}$ may be each independently one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{59}$ may be one of a phenyl group, a naphthyl group, an anthryl group, a biphenyl group, a pyridyl group; and a phenyl group, a naphthyl group, an anthryl group, a biphenyl group, and a pyridyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment the compound of Formula 300 may be a compound represented by Formula 300A below:

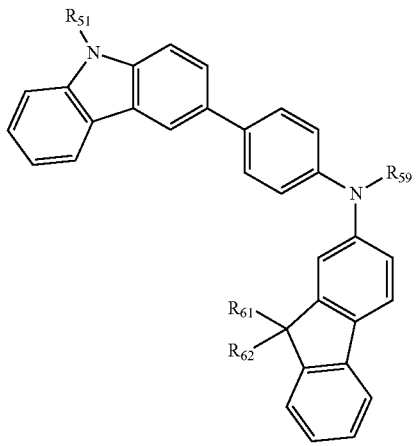

<Formula 300A>

In Formula 300A, $R_{51}$, $R_{60}$, $R_{61}$, and $R_{59}$ may be as defined above.

In some non-limiting embodiments, at least one of the HIL, HTL, and H-functional layer may include at least one of compounds represented by Formulae 301 to 320 below:

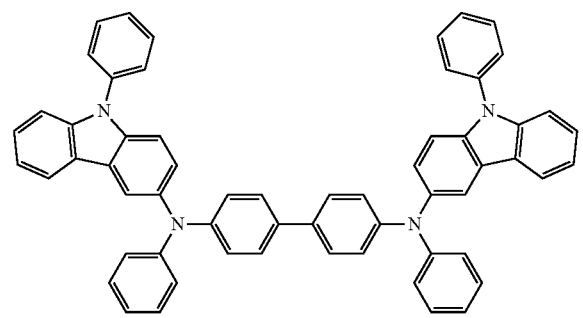

301

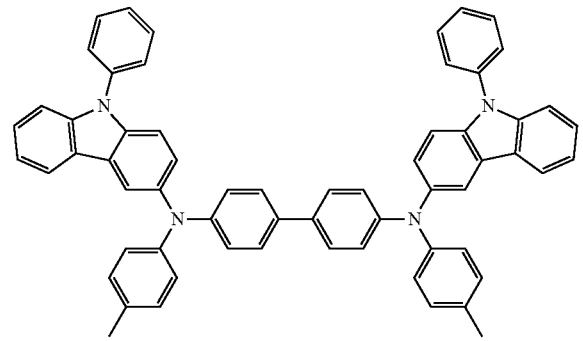

302

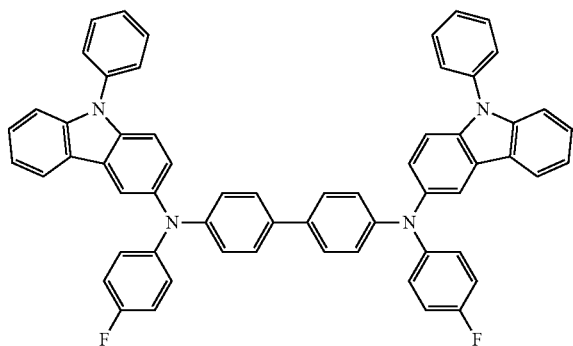
303
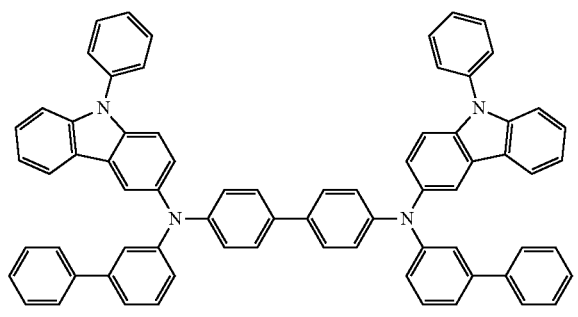
307
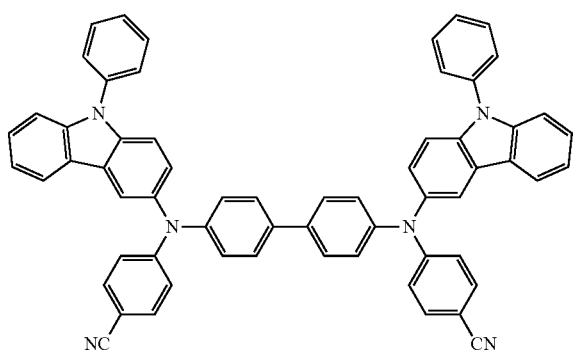
304
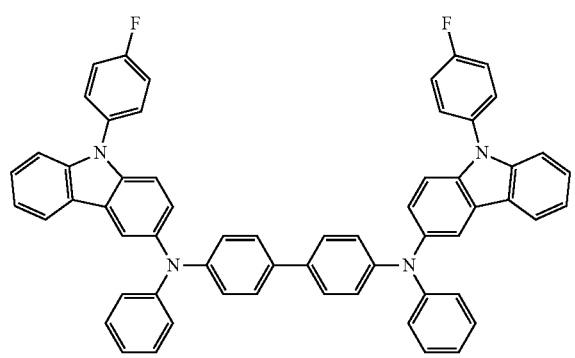
308
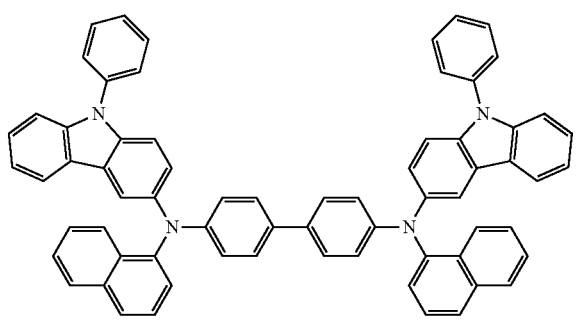
305
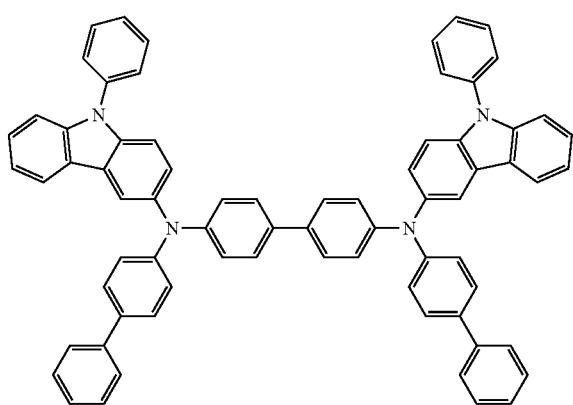
306
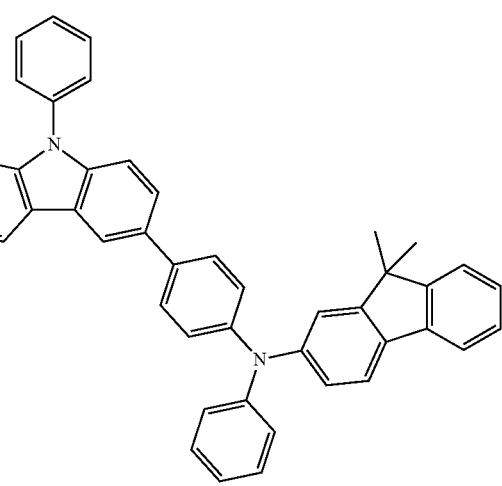
309

310
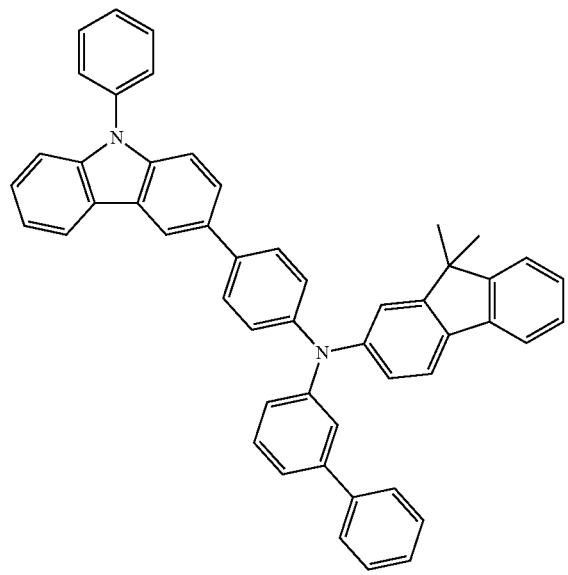
311
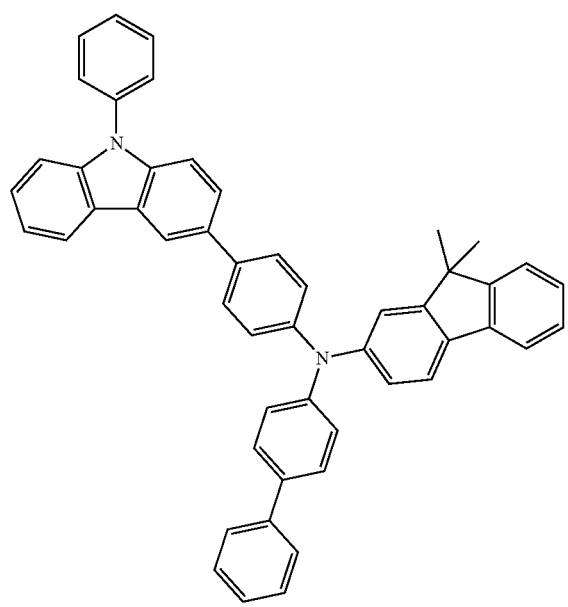
312
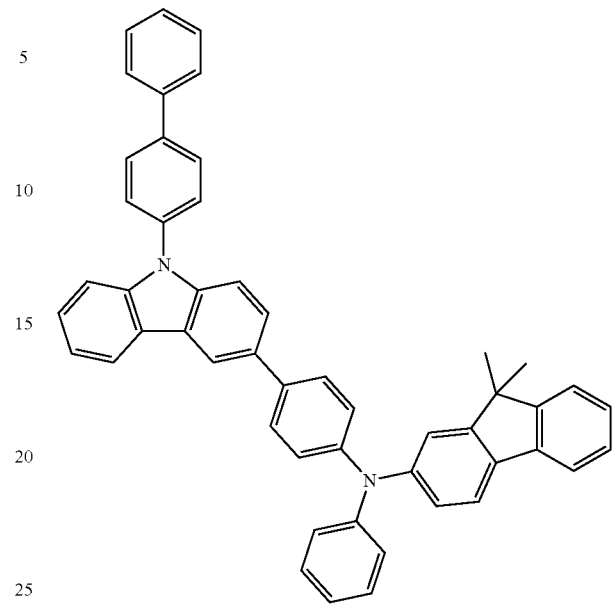
313
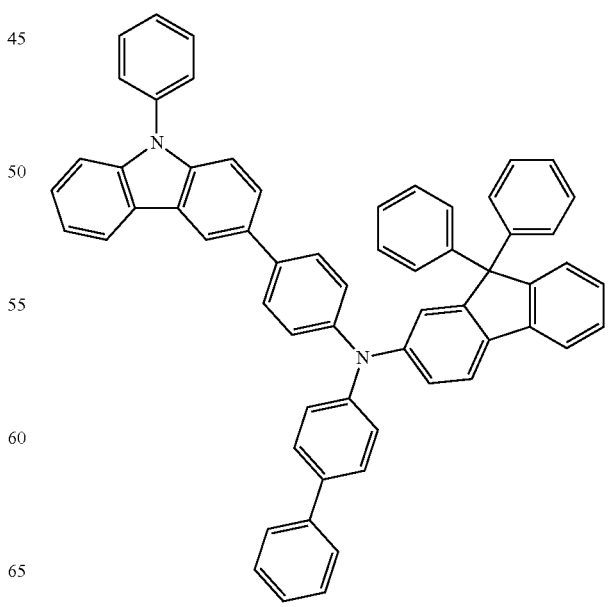

314
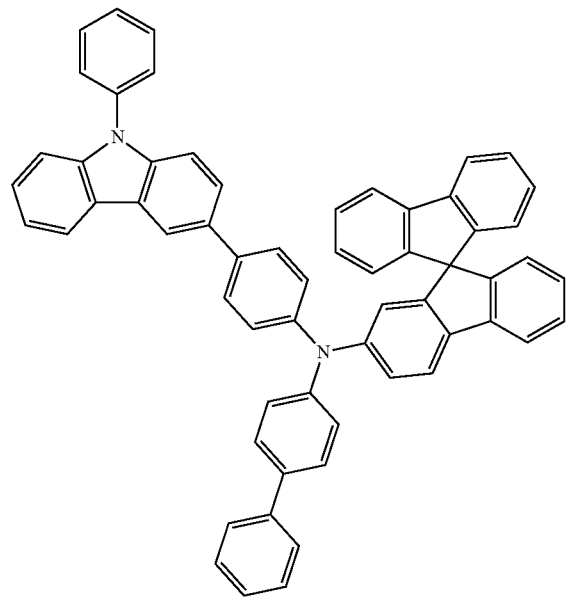
315
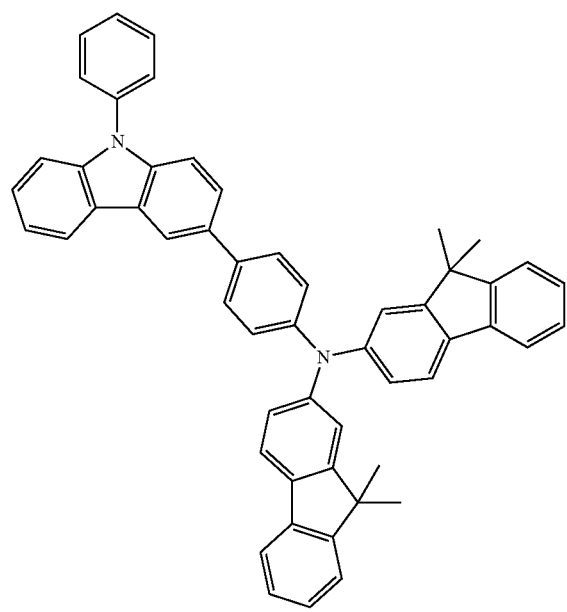
316
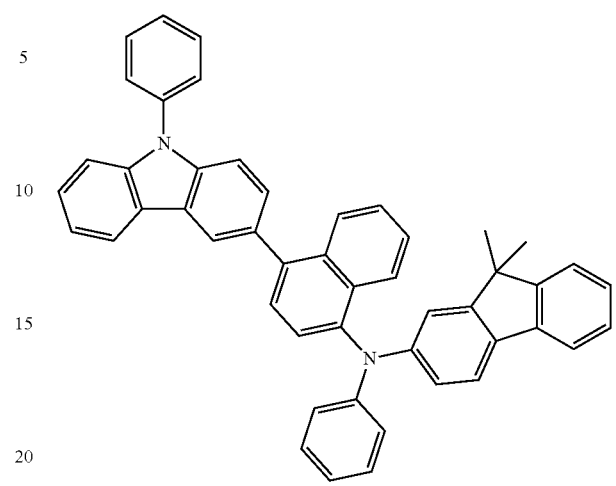
317
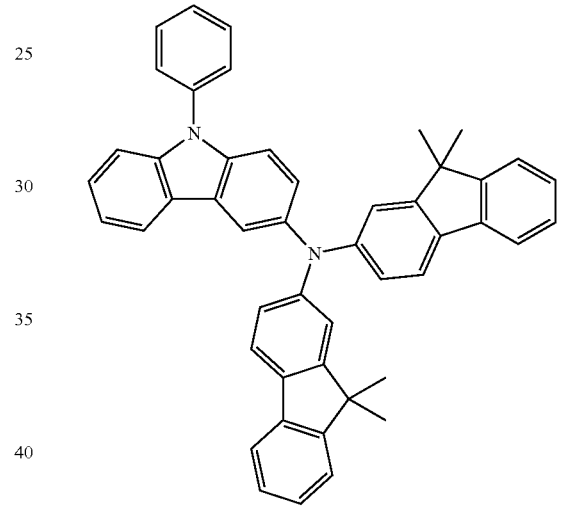
318
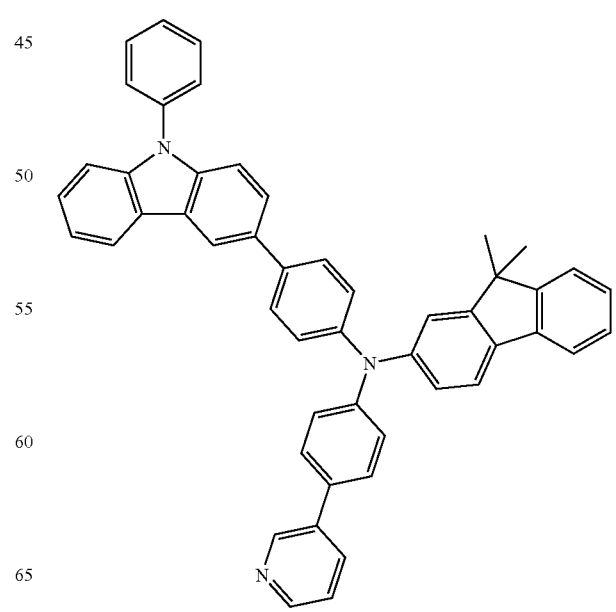

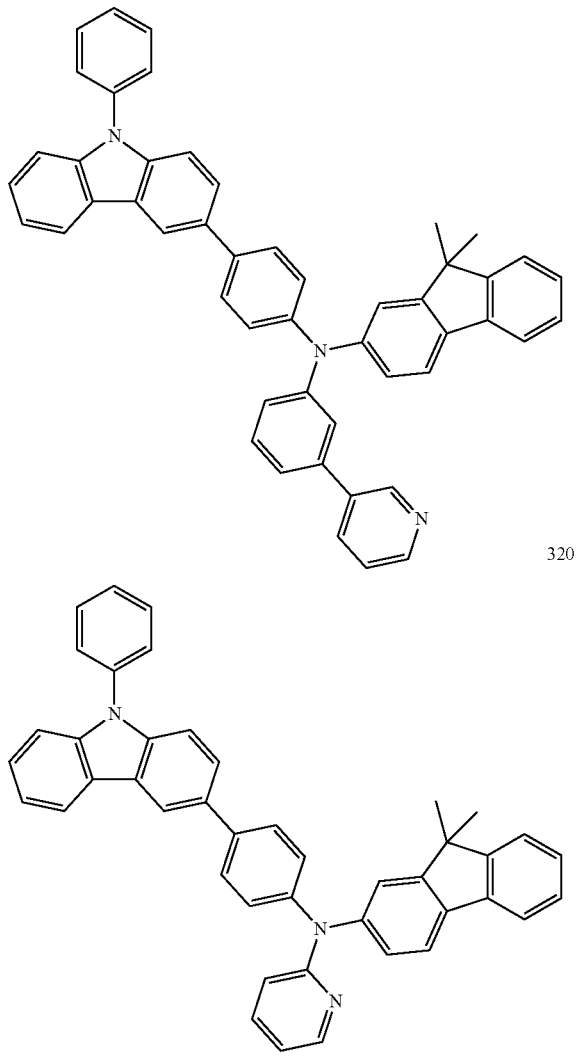

At least one of the HIL, HTL, and H-functional layer may further include a charge-generating material for improved layer conductivity, in addition to a known hole injecting material, hole transport material, and/or material having both hole injection and hole transport capabilities as described above.

The charge-generating material may be, for example, a p-dopant. The p-dopant may be one of quinine derivatives, metal oxides, and compounds with a cyano group, but are not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-CTNQ), and the like; metal oxides such as tungsten oxide, molybdenum oxide, and the like; and cyano-containing compounds such as Compound 200 below.

<Compound 200>

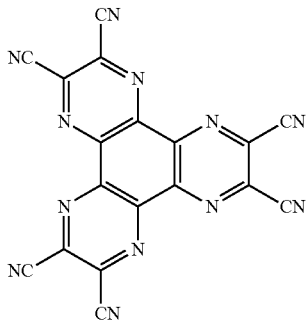

<F4-CTNQ>

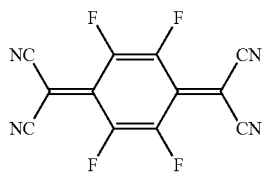

When the hole injection layer, hole transport layer, or H-functional layer further includes a charge-generating material, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The butter layer may include any hole injecting material or hole transporting material that are widely known. In some other embodiments, the buffer layer may include the same material as one of the materials included in the HIL, HTL, and H-functional layer that underly the buffer layer.

Then, an EML may be formed on the HTL, H-functional layer, or buffer layer by vacuum deposition, spin coating, casting, LB deposition, or the like. When the EML is formed using vacuum deposition or spin coating, the deposition and coating conditions may be similar to those for the formation of the HIL, though the conditions for deposition and coating may vary according to the material that is used to form the EML.

The EML may be formed using a variety of known light-emitting materials. In some embodiments, the EML may be formed using a known host and a dopant. Dopants that may be used to form the EML may include either a fluorescent dopant or a phosphorescent dopant which are widely known in the art.

Non-limiting examples of the host are Alq3, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, distyrylarylene (DSA), dmCBP (see a formula below), and Compounds 501 to 509 below.

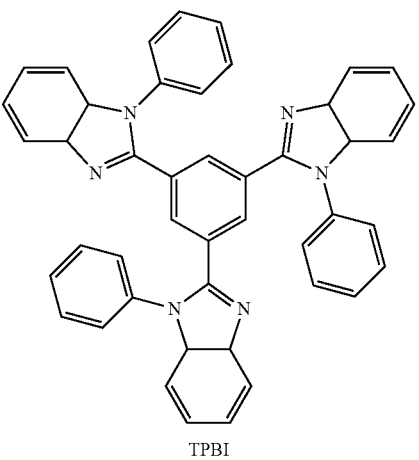

TPBI

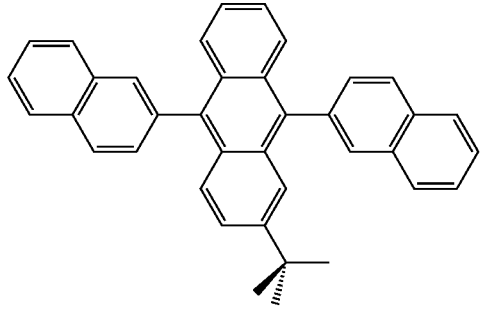
TBADN
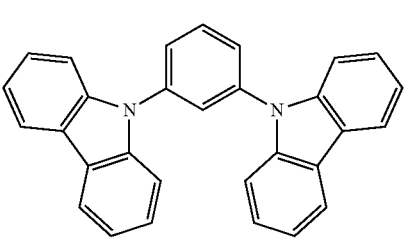
501
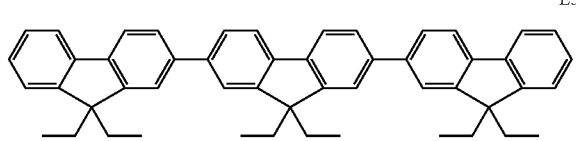
E3
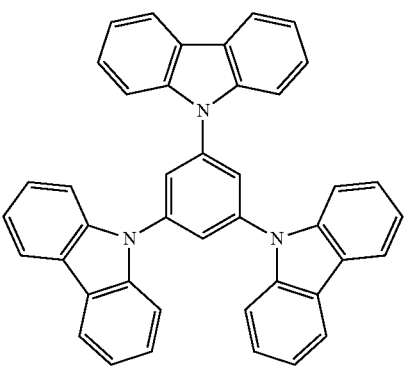
502
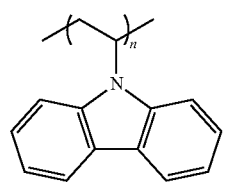
PVK
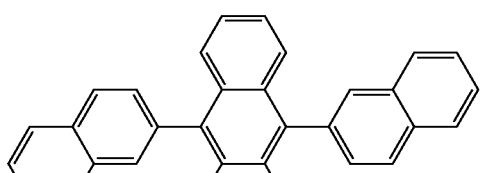
ADN
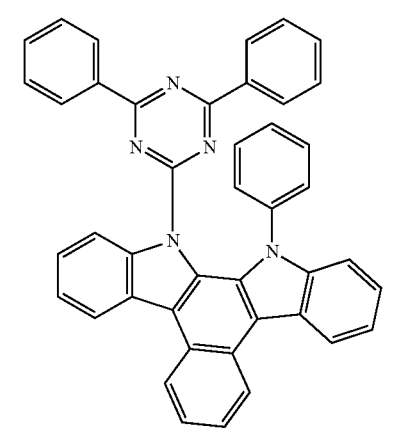
503
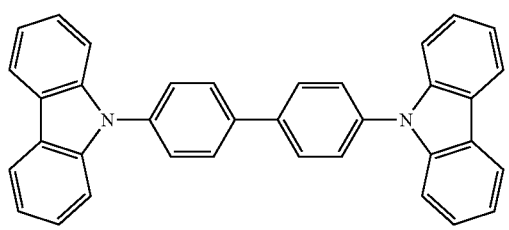
CBP
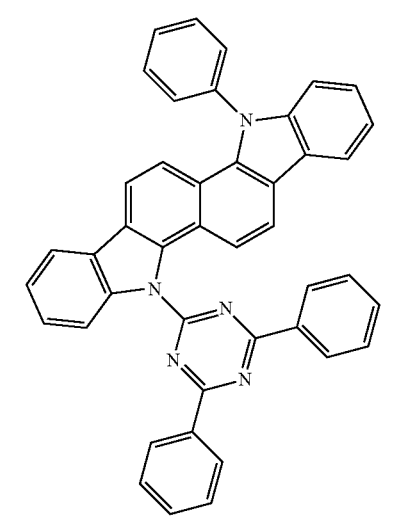
504
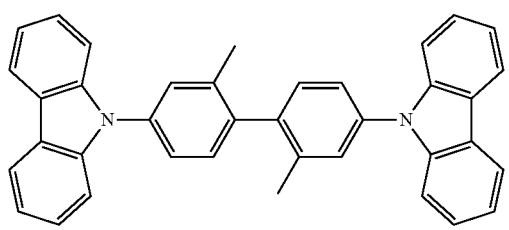
dmCBP

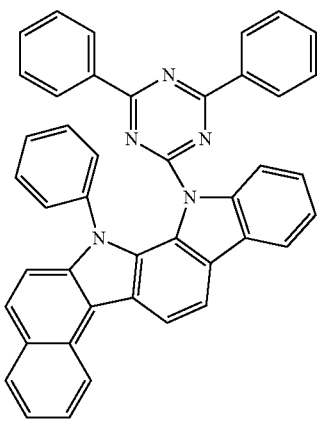

505

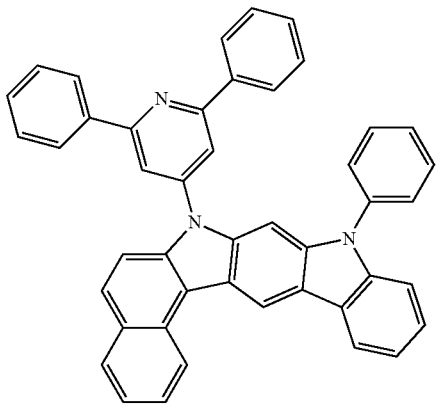

506

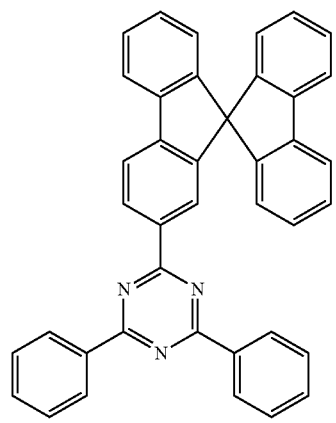

507

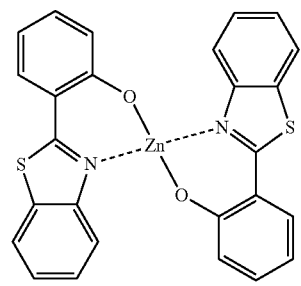

508

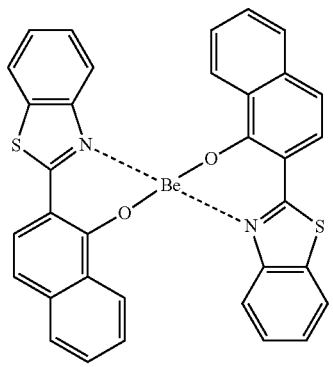

509

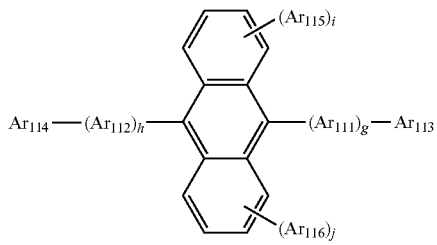

In some embodiments, an anthracene-based compound represented by Formula 400 below may be used as the host.

<Formula 400>

$$Ar_{114}-(Ar_{112})_h \cdots (Ar_{111})_g-Ar_{113}$$

with $(Ar_{115})_i$ and $(Ar_{116})_j$ substituents on the anthracene.

In Formula 400, $Ar_{111}$ and $Ar_{112}$ may be each independently a substituted or unsubstituted $C_5$-$C_{60}$arylene group; $Ar_{113}$ to $Ar_{116}$ may be each independently a substituted or unsubstituted $C_1$-$C_{10}$alkyl group, or a substituted or unsubstituted $C_5$-$C_{60}$aryl group; and g, h, i, and j may be each independently an integer from 0 to 4.

In some non-limiting embodiments, $Ar_{111}$ and $Ar_{112}$ in Formula 400 may be each independently a phenylene group, a naphthylene group, a phenanthrenylene group, or a pyrenylene group; or a phenylene group, a naphthylene group, a phenanthrenylene group, a fluorenyl group, or a pyrenylene group that are substituted with at least one of a phenyl group, a naphthyl group, and an anthryl group.

In Formula 400 above, g, h, I, and j may be each independently 0, 1, or 2.

In Formula 400, $Ar_{113}$ to $Ar_{116}$ may be each independently one of a $C_1$-$C_{10}$alkyl group that is substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of a deuterium atom, a halogen atom, a hydroxyl group, a cyano group, a nitro group, an amino group, an amidino group, a hydroxyrazine, a hydroxyrazone, a carboxyl group or a salt thereof, a sulfonic acid group or a salt thereof, a phosphoric acid group or a salt thereof, a $C_1$-$C_{60}$alkyl group, a $C_2$-$C_{60}$alkenyl group, a $C_2$-$C_{60}$alkynyl group, a $C_1$-$C_{60}$alkoxy group, a phenyl group, a naphthyl group, an anthryl group, a pyrenyl group, a phenanthrenyl group, and a fluorenyl group; and

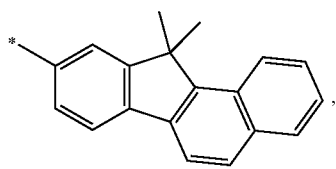 [SMILES: Cc1ccc2c(c1)C(C)(C)c1c-2ccc2ccccc12]
but are not limited thereto.
For example, the anthracene-based compound of Formula 400 above may be one of the compounds represented by the following formulae, but is not limited thereto:
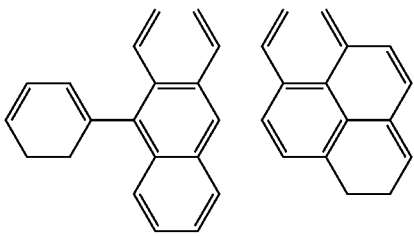
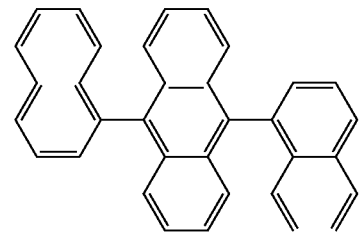
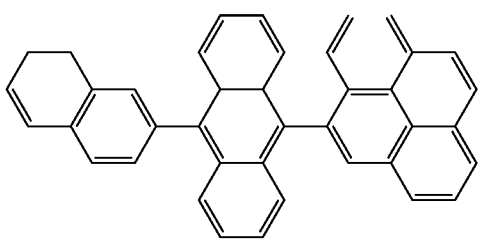
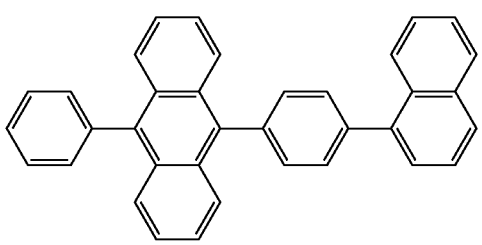
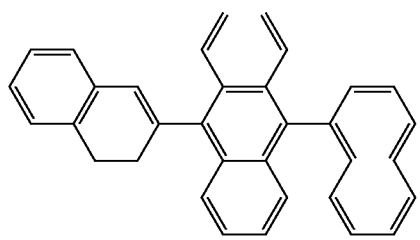
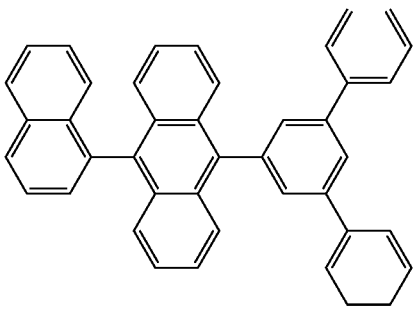
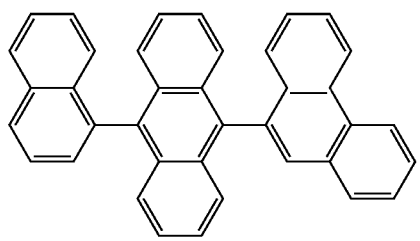
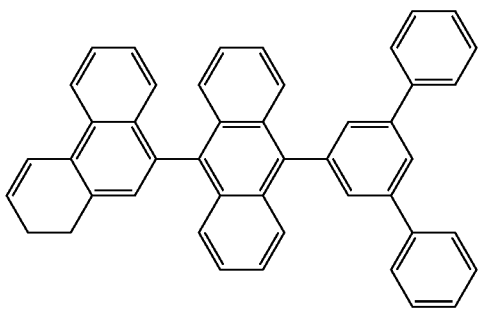
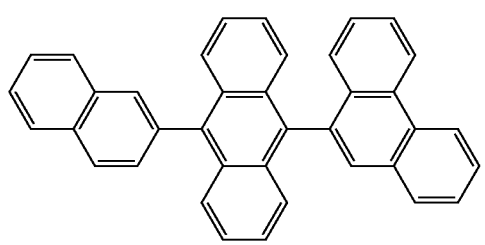
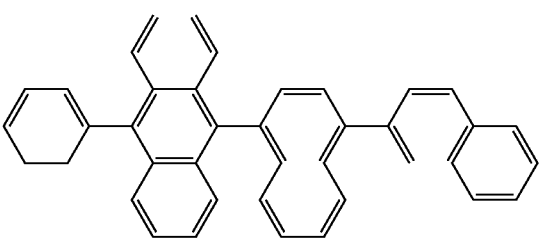
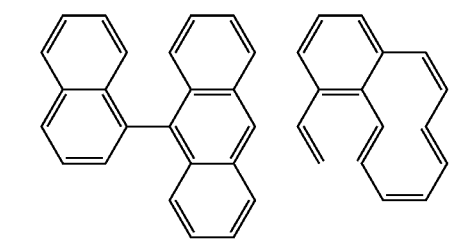

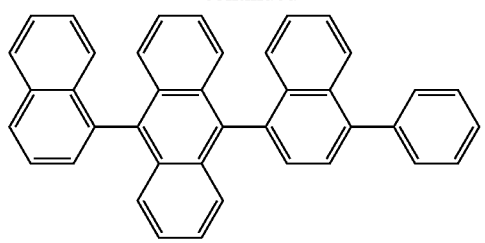
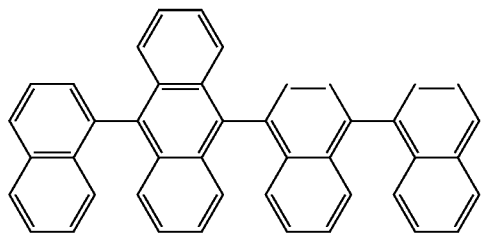
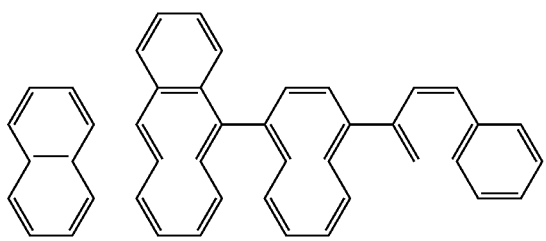
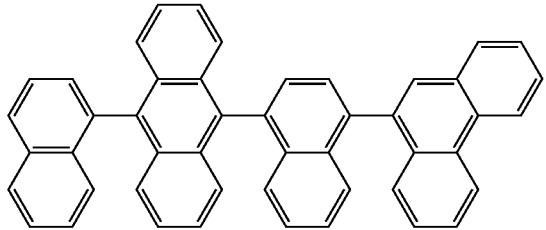
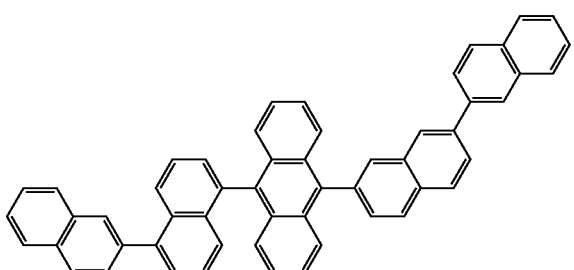
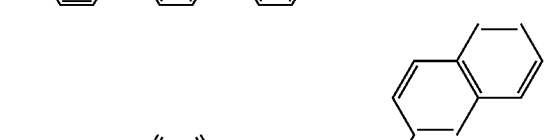
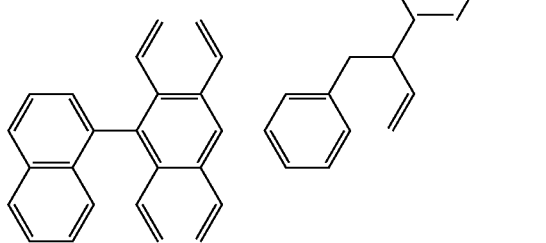
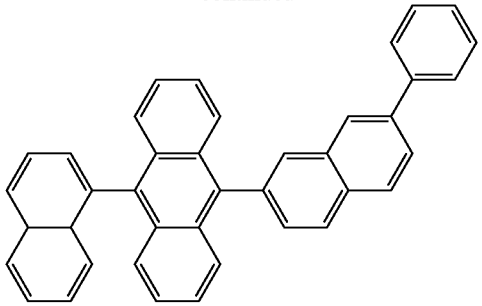
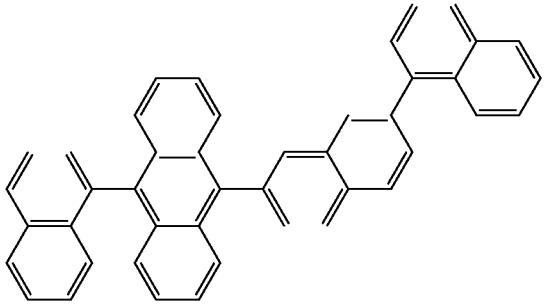
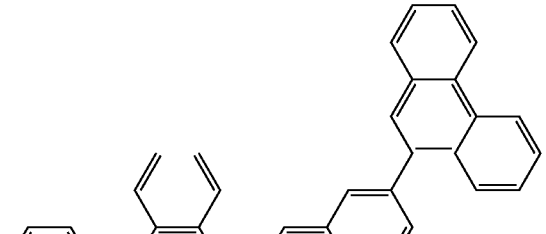
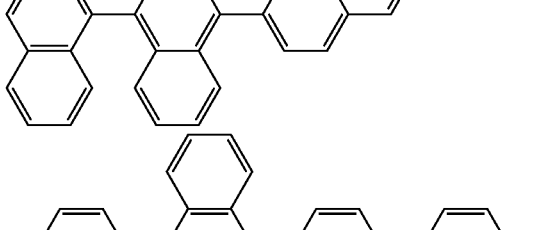
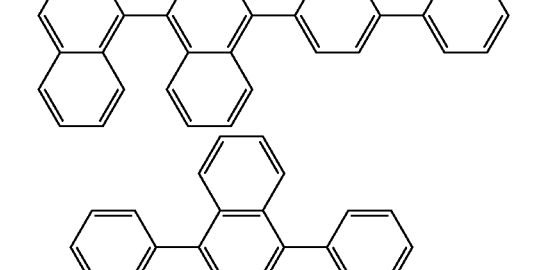
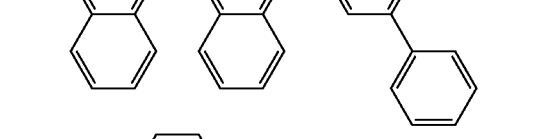
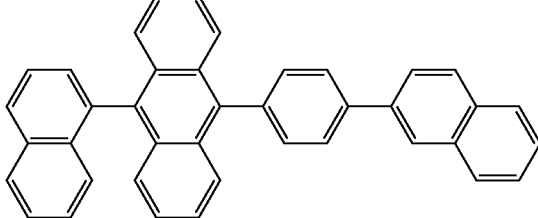

47
-continued
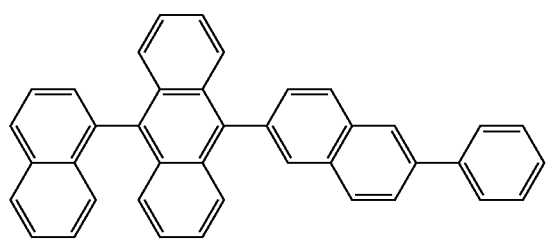
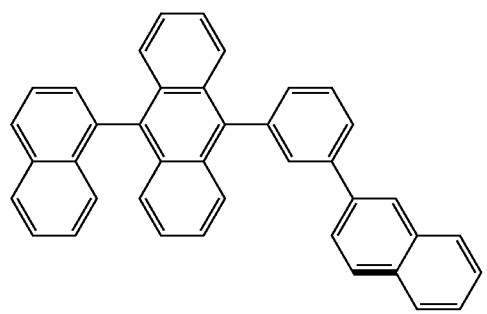
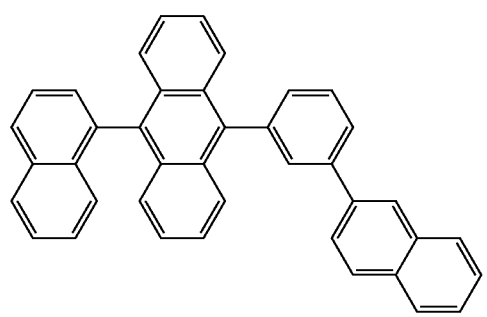
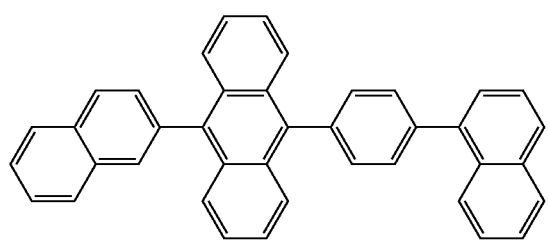
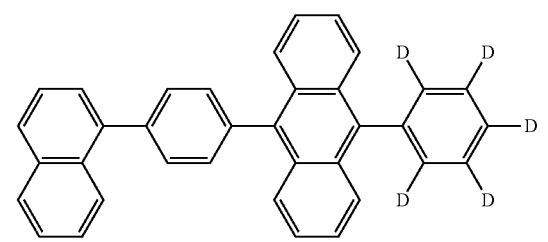
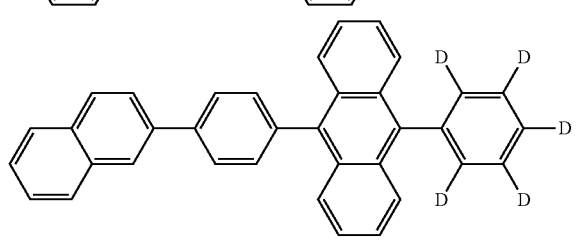
48
-continued
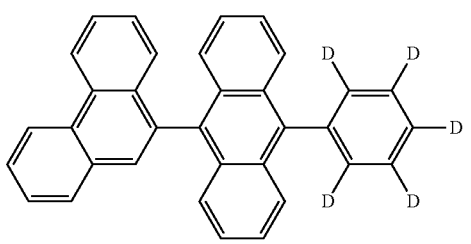
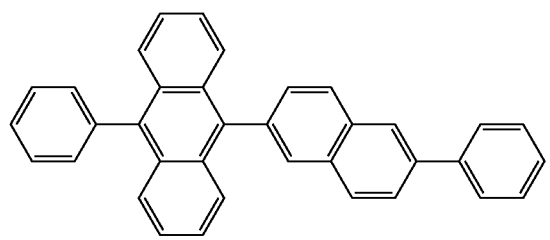
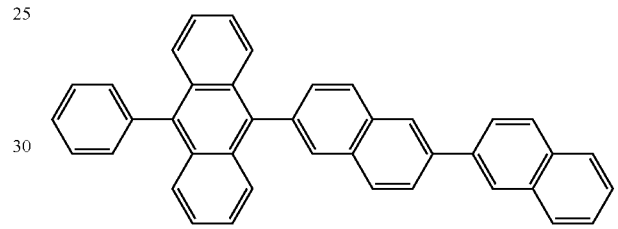
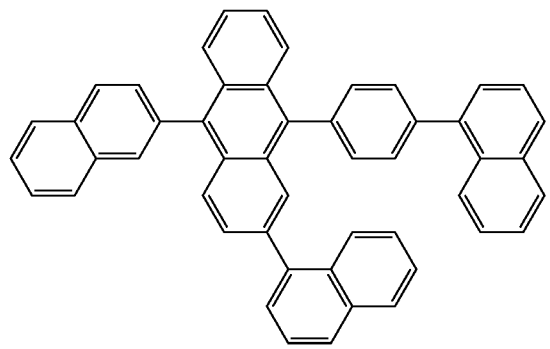
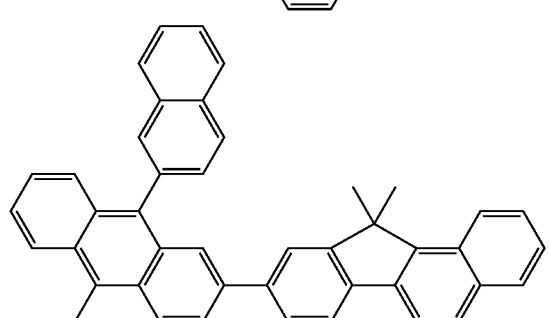
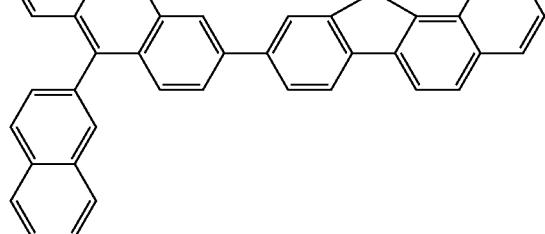

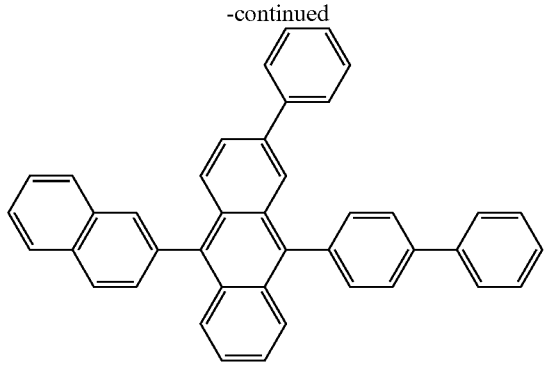

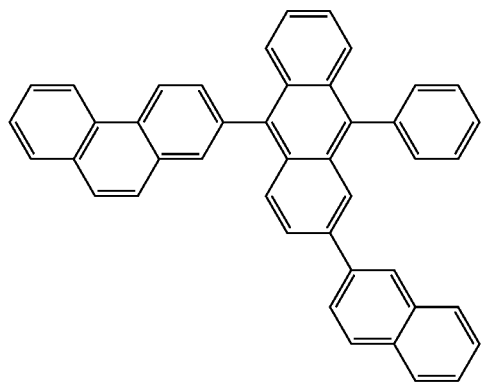 [SMILES: c1ccc(-c2c3ccccc3c(-c3ccc4c(ccc5ccccc54)c3)c3ccc(-c4ccc5ccccc5c4)cc23)cc1]

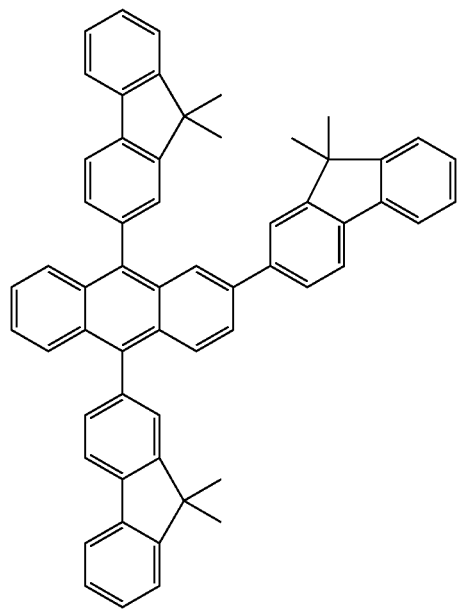

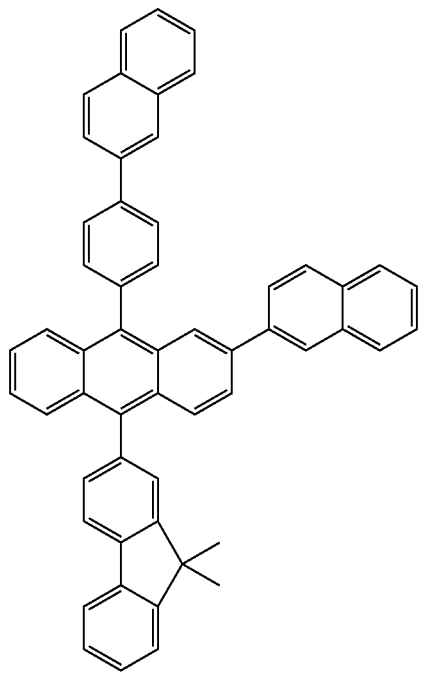

In some embodiments, an anthracene-based compound represented by Formula 401 below may be used as the host:

<Formula 401>

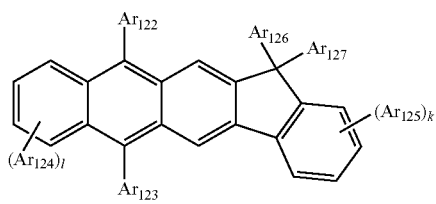

$Ar_{122}$ to $Ar_{125}$ in Formula 401 above may be defined as described above in conjunction with $Ar_{113}$ of Formula 400, and thus detailed descriptions thereof will not be provided here.

$Ar_{126}$ and $Ar_{127}$ in Formula 401 above may be each independently a C1-$C_{10}$ alkyl group, for example, a methyl group, an ethyl group, or a propyl group.

In Formula 401, k and l may be each independently an integer from 0 to 4, for example, 0, 1, or 2.

For example, the anthracene-based compound of Formula 401 above may be one of the compounds represented by the following formulae, but is not limited thereto:

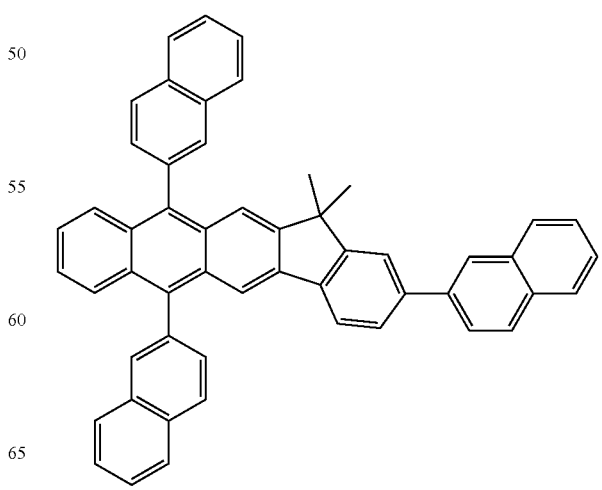

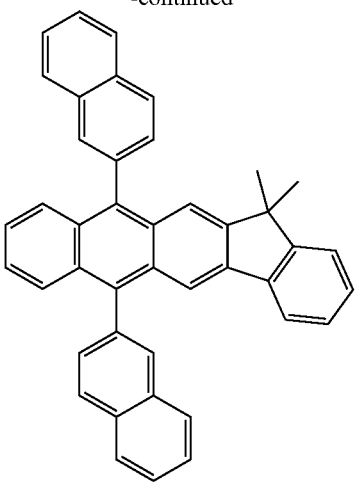

When the organic light-emitting device is a full color organic light-emitting device, the emission layer may be patterned into a red emission layer, a green emission layer, and a blue emission layer.

At least one of the red EML, the green EML, and the blue EML may include a dopant below (ppy=phenylpyridine).

Non-limiting examples of the blue dopant are compounds represented by the following formulae.

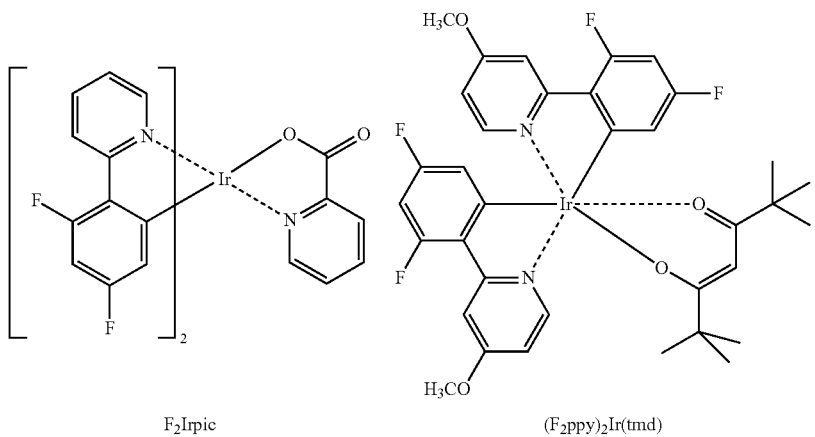

-continued
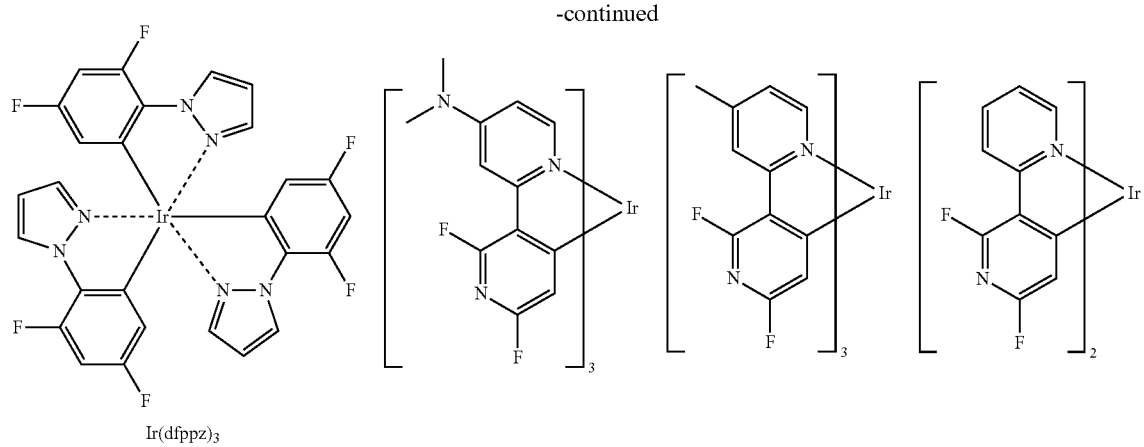
Ir(dfppz)₃
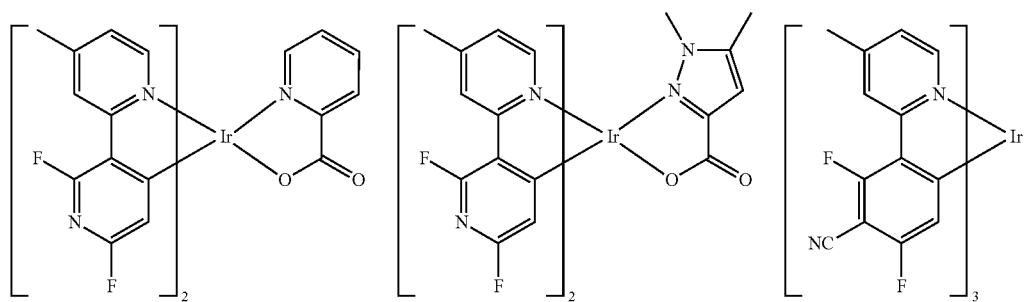
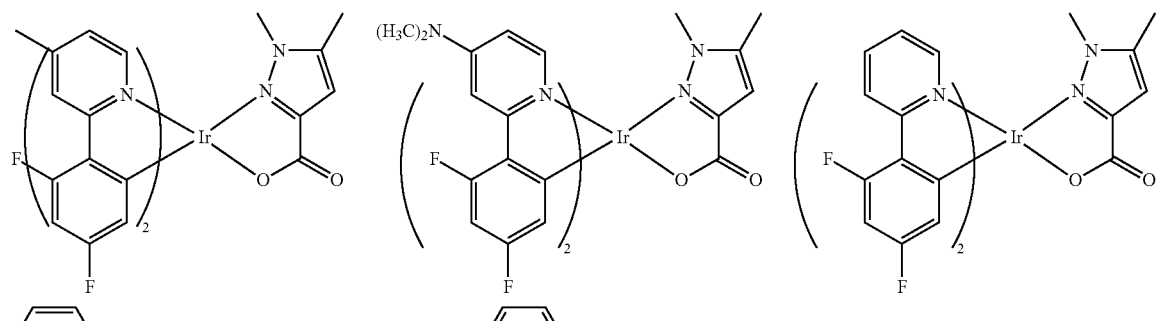
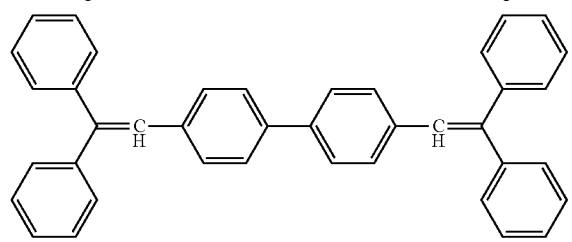
DPVBi
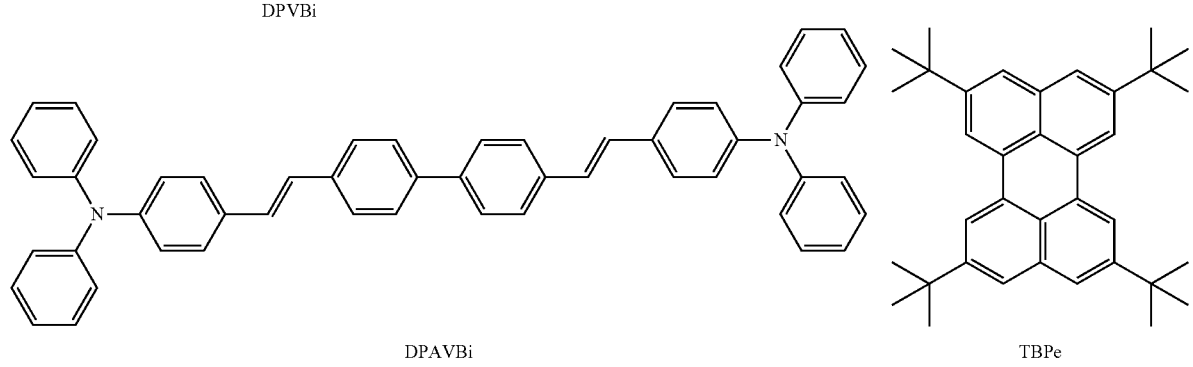
DPAVBi
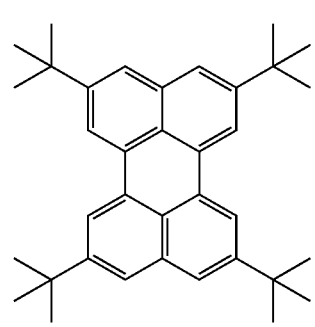
TBPe Non-limiting examples of the red dopant are compounds represented by the following formulae.
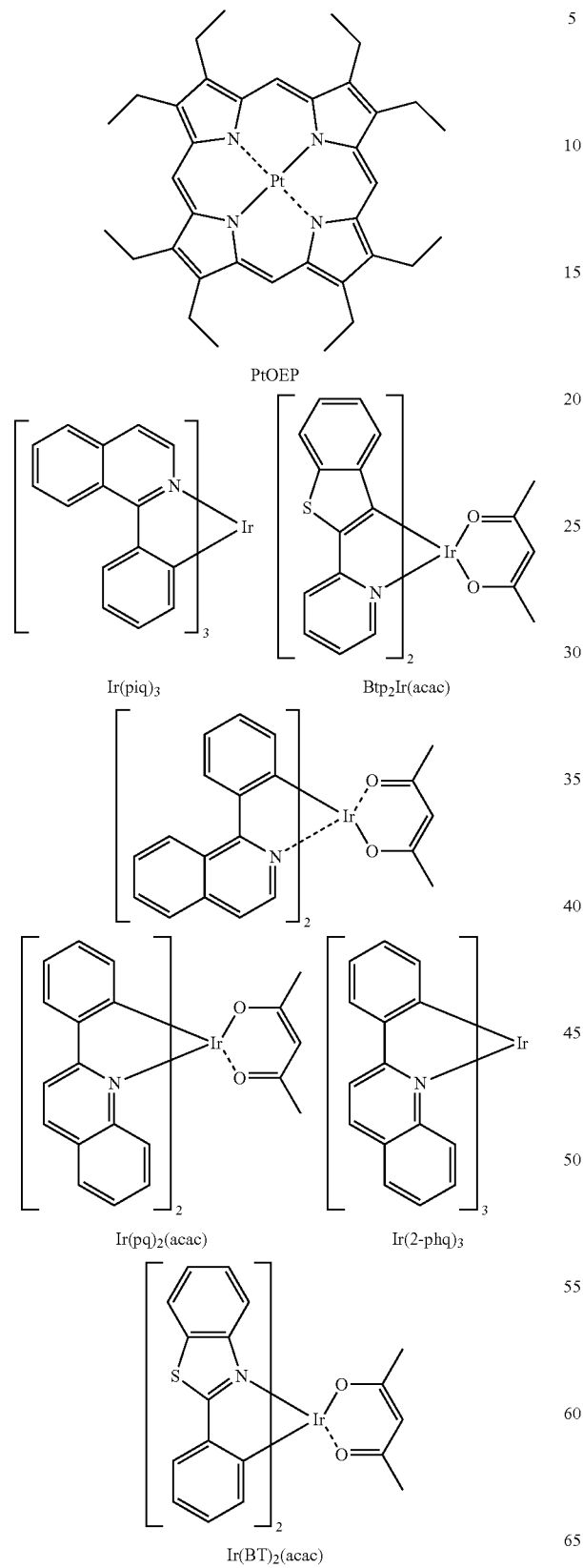
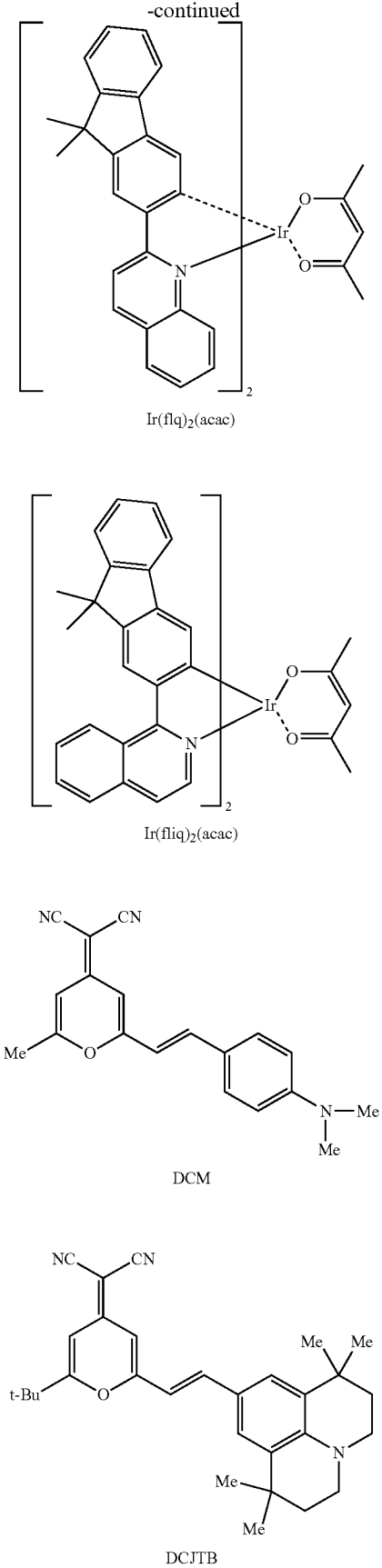

Non-limiting examples of the green dopant are compounds represented by the following formulae.
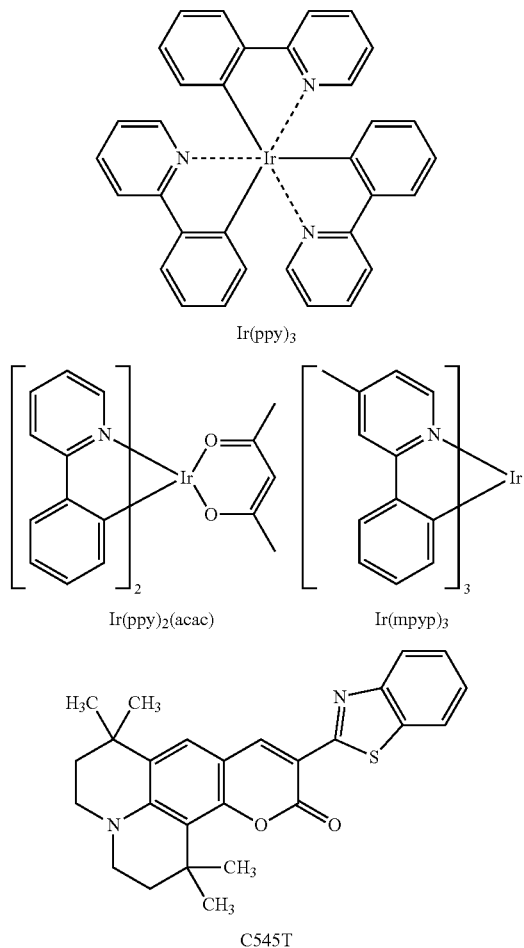
Non-limiting examples of the dopant that may be used in the EML are Pt complexes represented by the following formulae:
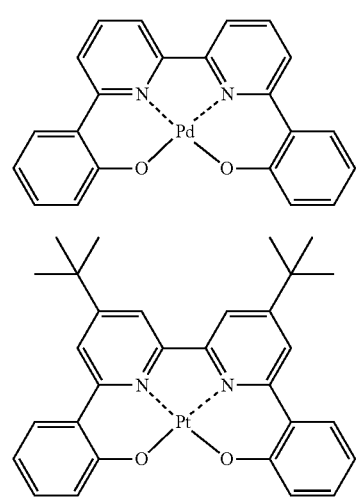
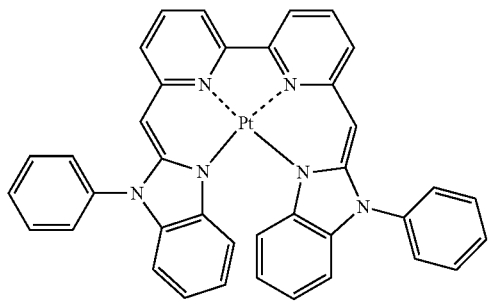
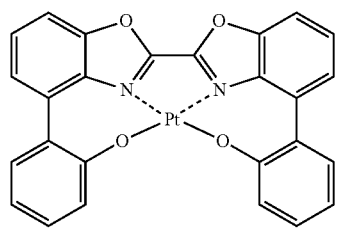
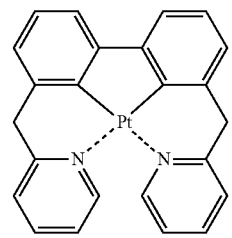
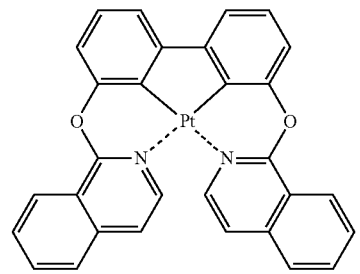
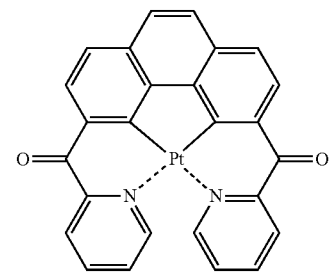
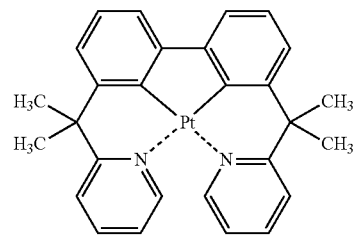

D9 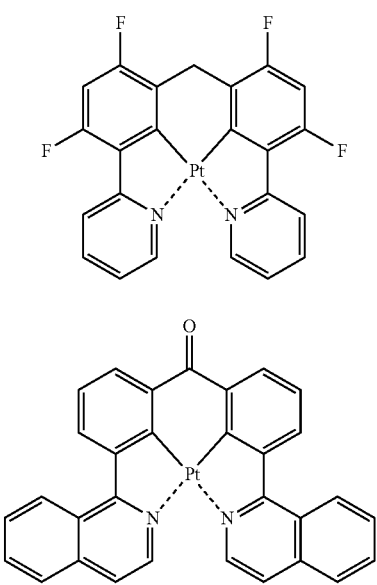
D10 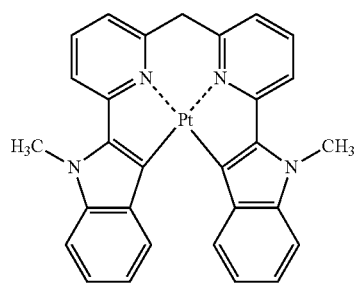
D11 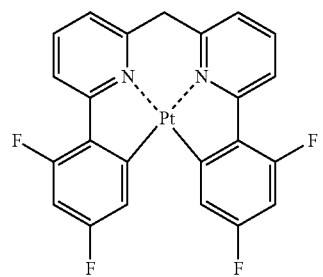
D12 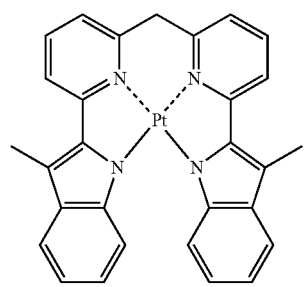
D13
D14 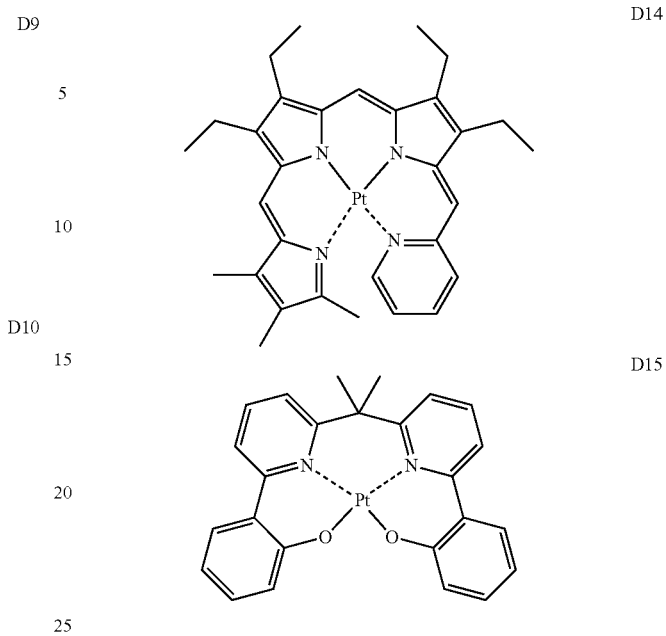
D15 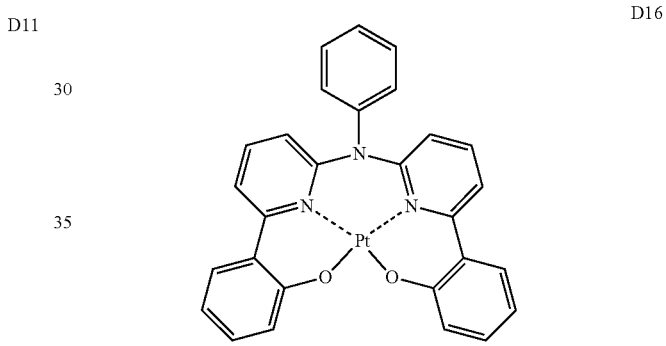
D16 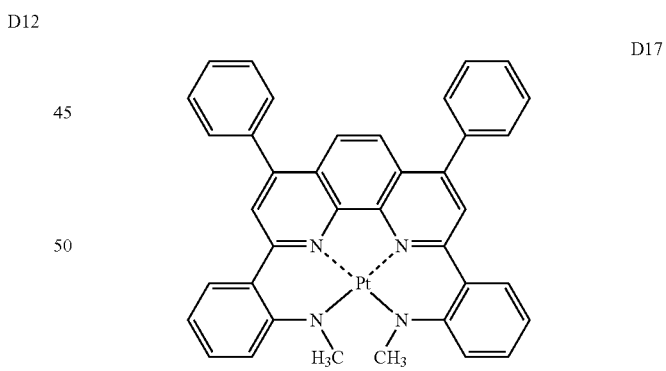
D17 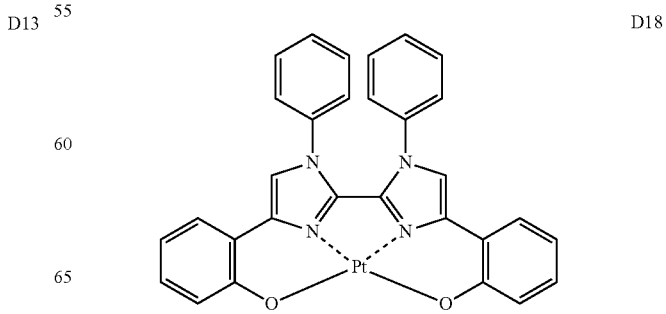
D18

D19 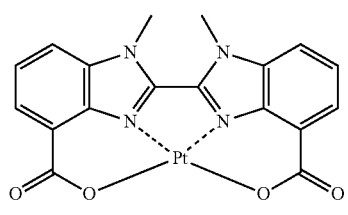
D20 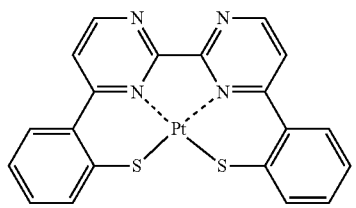
D21 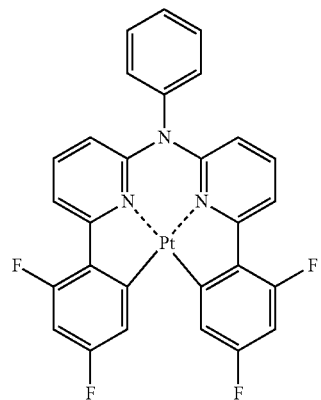
D22 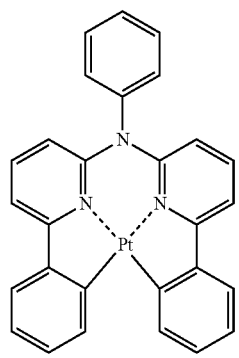
D23 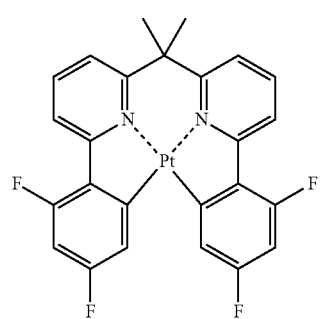
D24 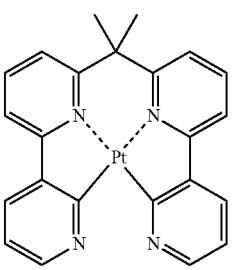
D25 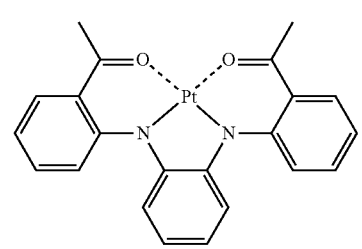
D26 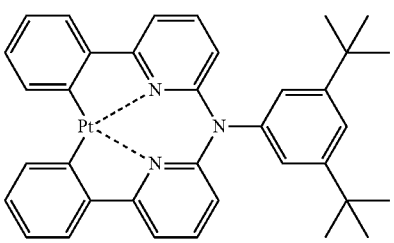
D27 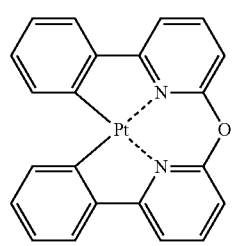
D28 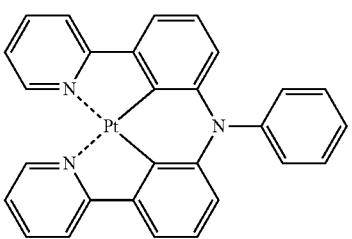
D29 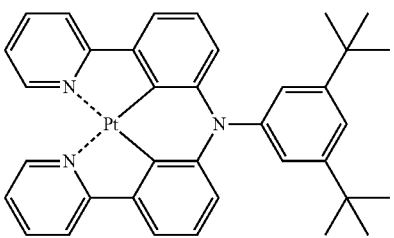

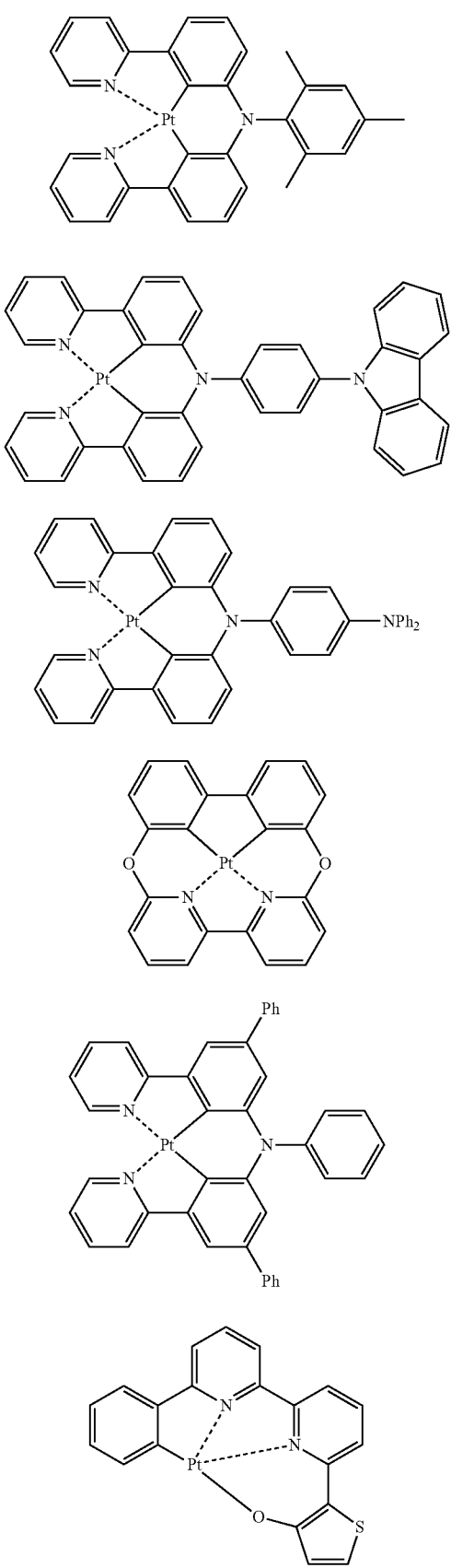
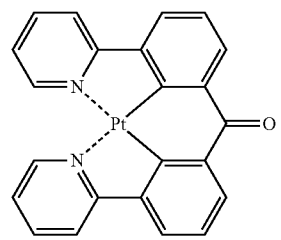
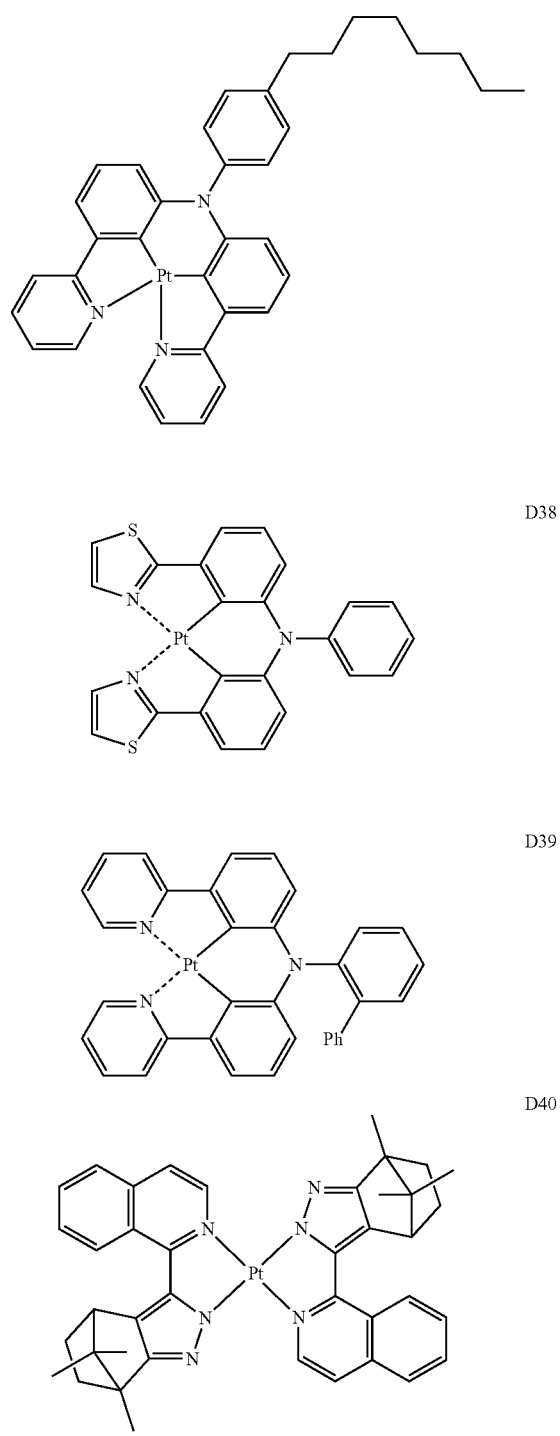

-continued
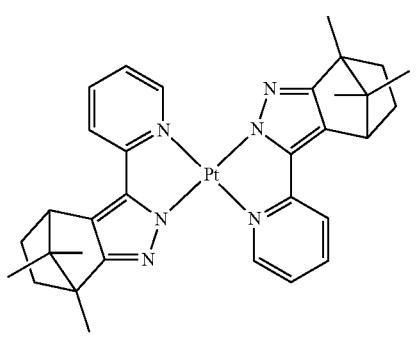 D41
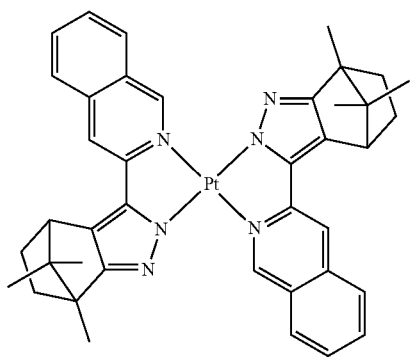 D42
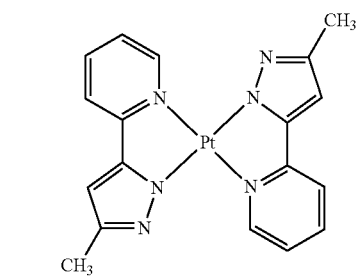 D43
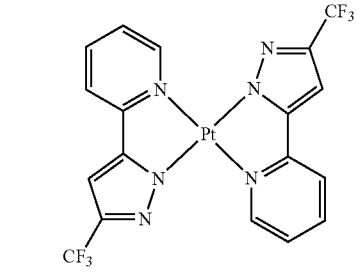 D44
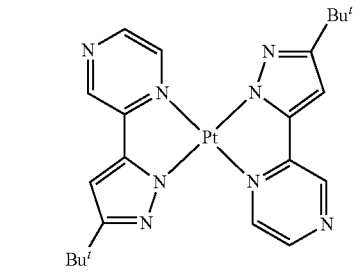 D45
-continued
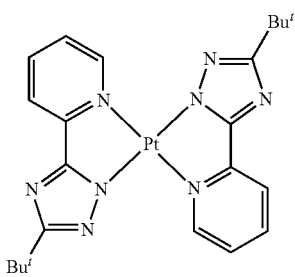 D46
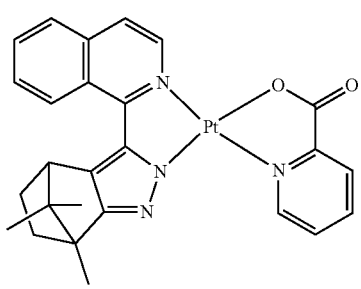 D47
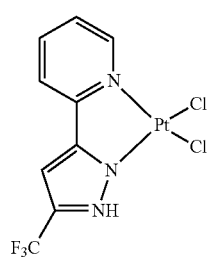 D48
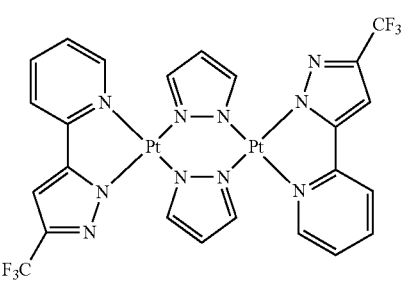 D49
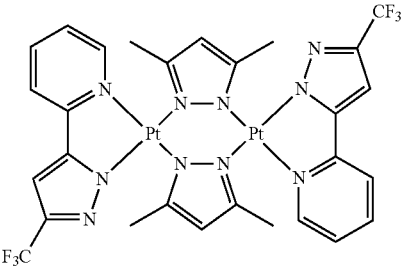 D50

Non-limiting examples of the dopant that may be used in the EML are Os complexes represented by the following formulae:

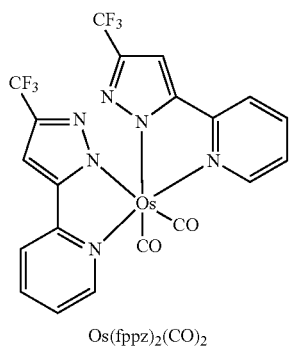

Os(fppz)$_2$(CO)$_2$

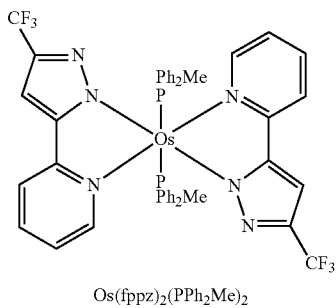

Os(fppz)$_2$(PPh$_2$Me)$_2$

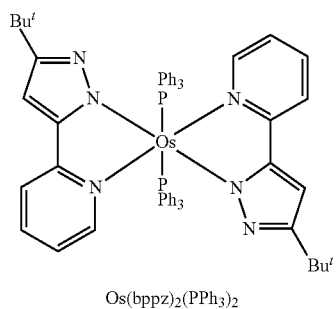

Os(bppz)$_2$(PPh$_3$)$_2$

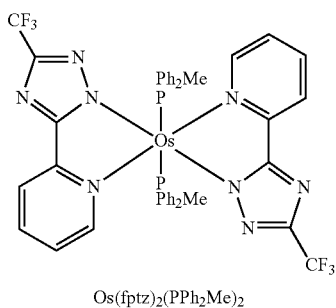

Os(fptz)$_2$(PPh$_2$Me)$_2$

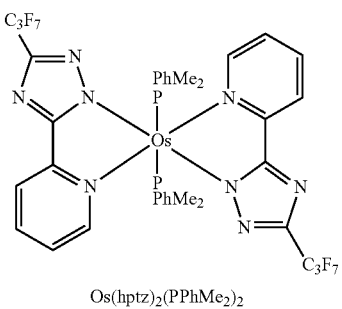

Os(hptz)$_2$(PPhMe$_2$)$_2$

When the EML includes both a host and a dopant, the amount of the dopant may be from about 0.01 to about 15 parts by weight based on 100 parts by weight of the host. However, the amount of the dopant is not limited to this range.

The thickness of the EML may be from about 100 Å to about 1000 Å, and in some embodiments, from about 200 Å to about 600 Å. When the thickness of the EML is within these ranges, the EML may have good light emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary according to a compound that is used to form the ETL. A material for forming the ETL may be the compound of Formula 1 above or any known material that can stably transport electrons injected from an electron injecting electrode (cathode). Non-limiting examples of materials for forming the ETL are a quinoline derivative, such as tris(8-quinolinorate)aluminum (Alq3), TAZ, BAlq, beryllium bis(benzoquinolin-10-olate) (Bebq$_2$), 9,10-di(naphthalene-2-yl)anthracene (ADN), Compound 201, and Compound 202, but are not limited thereto.

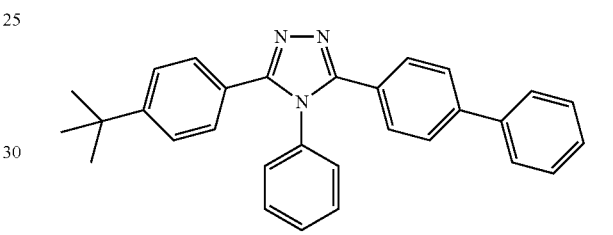

TAZ

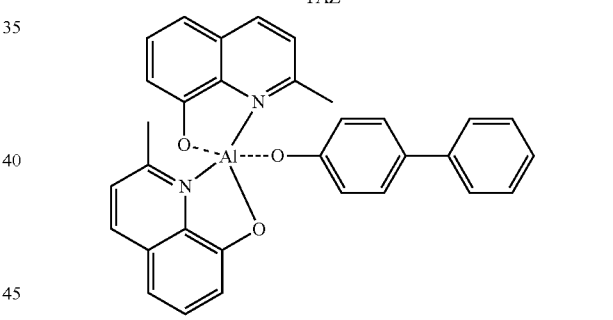

BAlq

<Compound 201>

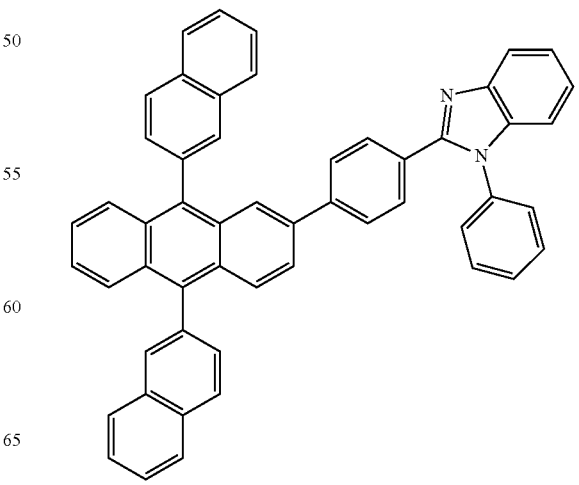

<Compound 202>

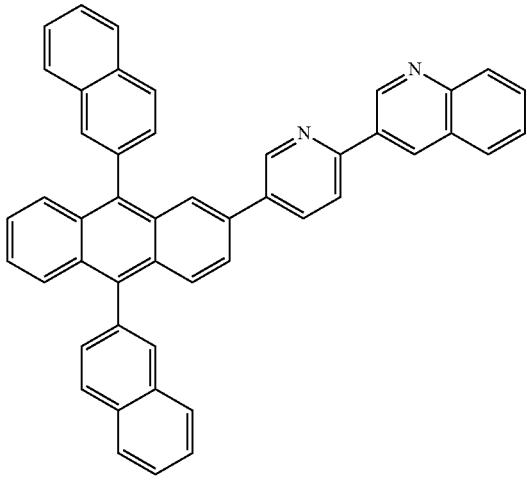

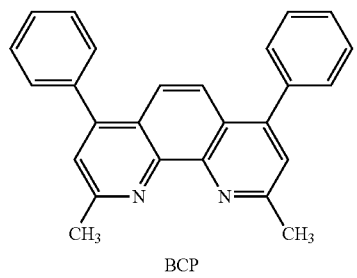

BCP

The thickness of the HTL may be from about 100 Å to about 1000 Å, and in some embodiments, from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to any known electron-transporting organic compound.

The metal-containing material may include a lithium (Li) complex. Non-limiting examples of the Li complex are lithium quinolate (LiQ) and Compound 203 below:

<Compound 203>

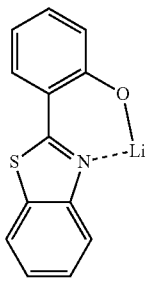

Then, an EIL, which facilitates injection of electrons from the cathode, may be formed on the ETL. Any suitable electron-injecting material may be used to form the EIL.

Non-limiting examples of materials for forming the EIL are LiF, NaCl, CsF, $Li_2O$, and BaO, which are known in the art. The deposition and coating conditions for forming the EIL 18 may be similar to those for the formation of the HIL, though the deposition and coating conditions may vary according to the material that is used to form the EIL 18.

The thickness of the EIL may be from about 1 Å to about 100 Å, and in some embodiments, from about 3 Å to about 90 Å. When the thickness of the EIL is within these ranges, the EIL may have satisfactory electron injection ability without a substantial increase in driving voltage.

Finally, the second electrode is disposed on the organic layer. The second electrode may be a cathode that is an electron injection electrode. material for forming the second electrode may be a metal, an alloy, an electro-conductive compound, which have a low work function, or a mixture thereof. In this regard, the second electrode may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting device, the transmission electrode may be formed of indium tin oxide (ITO) or indium zinc oxide (IZO).

Although the organic light-emitting device of FIG. 1 is described above, the present invention is not limited thereto.

When a phosphorescent dopant is used in the EML, a HBL may be formed between the HTL and the EML or between the H-functional layer and the EML by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any known hole-blocking material may be used. Non-limiting examples of hole-blocking materials are oxadiazole derivatives, triazole derivatives, and phenanthroline derivatives. For example, bathocuproine (BCP) represented by the following formula may be used as a material for forming the HBL.

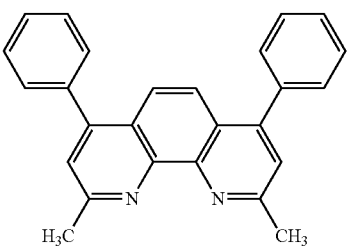

BCP

The thickness of the HBL may be from about 20 Å to about 1000 Å, and in some embodiments, from about 30 Å to about 300 Å. When the thickness of the HBL is within these ranges, the HBL may have improved hole blocking ability without a substantial increase in driving voltage.

According to embodiments of the present invention, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

In some embodiments the organic layer of the organic light-emitting device may be formed of the compound of Formula 1 by using a deposition method or may be formed using a wet method of coating a solution of the compound of Formula 1.

Hereinafter, the present invention will be described in detail with reference to the following synthesis examples and other examples. However, these examples are for illustrative purposes only and are not intended to limit the scope of the present invention.

EXAMPLES

Synthesis Example 1;

Synthesis of Compound 3

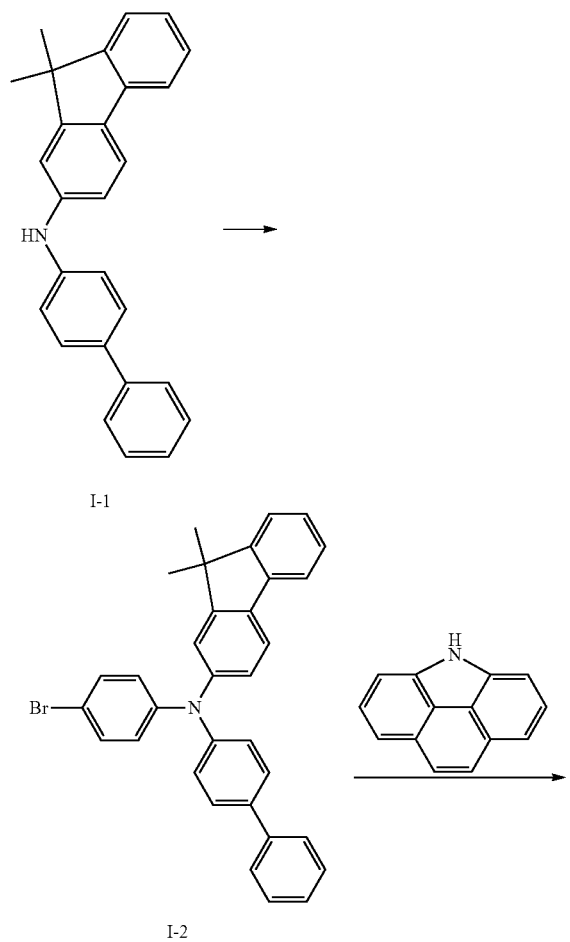

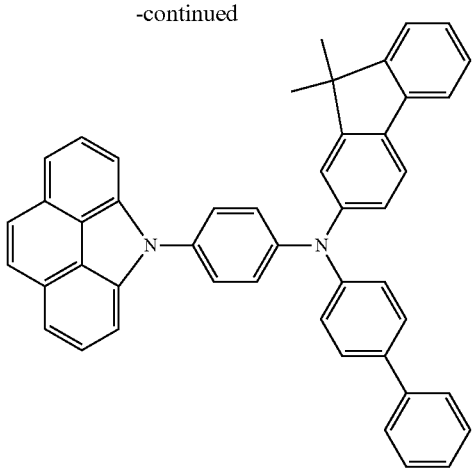

Synthesis of Intermediate I-2

10.8 g (30.0 mmol) of compound I-1, 5.64 g (20.0 mmol) of 4-bromo-1-iodobenzene, 0.36 g (0.4 mmol) of $Pd_2(dba)_3$, 0.04 g (0.4 mmol) of $PtBu_3$, and 4.14 g (30.0 mmol) of KOtBu were dissolved in 70 mL of toluene, and then stirred at about 85° C. for about 4 hours. The reaction solution was cooled to room temperature, and then extracted three times with 60 mL of water and 60 mL of diethylether. The organic phase was collected and was dried using magnesium sulfate to evaporate the solvent. The residue was separated and purified using silica gel column chromatography to obtain 7.12 g of Intermediate I-2 (yield: 69%). This compound was identified using LC-MS. $C_{33}H_{26}BrN$ $M^+$ 515.1

Synthesis of Compound 3

5.16 g (10.0 mmol) of Intermediate I-2, 1.91 g (10.0 mmol) of 6H-benzo[def]carbazole, 0.18 g (1.0 mmol) of 1,10-phenanthroline, 0.38 g (2.0 mmol) of CuI, and 4.14 g (30.0 mmol) of $K_2CO_3$ were dissolved in 30 mL of N,N-dimethylformamide (DMF), and then stirred at about 80° C. for about 24 hours. The reaction solution was cooled to room temperature, and then extracted three times with 30 mL of water and 40 mL of diethylether. The organic phase was collected and was dried using magnesium sulfate to evaporate the solvent. The residue was separated and purified using silica gel column chromatography to obtain 4.95 g of Compound 3 (yield: 79%). This compound was identified using MS/FAB and $^1$H-NMR. $C_{47}H_{34}N_2$ cal. 626.27. found 627.31

$^1$H NMR (CDCl$_3$, 400 MHz) • • 7.78-7.76 (m, 3H), 7.65-7.61 (m, 2H), 7.56-7.39 (m, 12H), 7.35-7.32 (m, 1H), 7.24-

7.20 (m, 2H), 7.14-7.10 (m, 2H), 7.08-7.04 (m, 2H), 7.02-6.98 (m, 1H), 6.83-6.79 (m, 2H), 6.72 (d, 1H), 1.65 (s, 6H)

Synthesis Example 2;

Synthesis of Compound 24

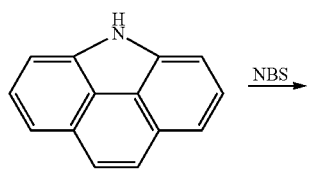

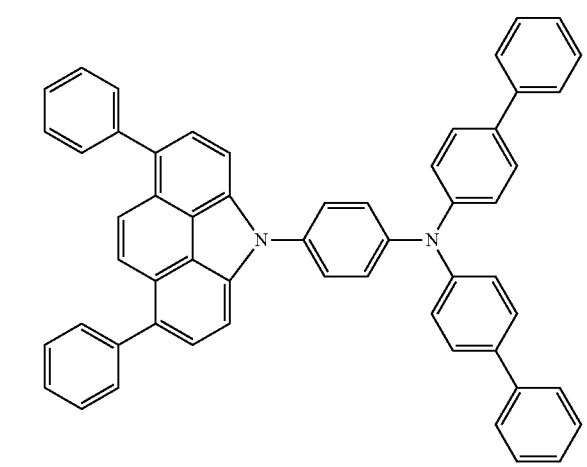

Synthesis of Intermediate I-3

7.82 g (44.0 mmol) of N-bromosuccinimide was added to a solution including 3.82 g (20.0 mmol) of 6H-benzo[def]carbazole that is completely dissolved in 100 mL of carbon tetrachloride (CCl$_4$), and then stirred at about 80° C. for about 30 minutes. The reaction solution was cooled to room temperature, and then stirred for about 30 minutes to precipitate crystals. The crystals were collected using a filter under reduced pressure, and then washed with methanol to obtain 3.82 g of Intermediate I-3 as white crystals (yield: 55%). This compound was identified using LC-MS. C$_{14}$H$_7$Br$_2$N; M$^+$346.9

Synthesis of Intermediate I-4

3.49 g (10.0 mmol) of Intermediate I-3, 2.68 g (22.0 mmol) of phenyl boronic acid, 1.15 g (1.0 mmol) of Pd(PPh$_3$)$_4$, and 4.14 g (30.0 mmol) of K$_2$CO$_3$ were dissolved in 40 mL of a mixed solvent of THF/H$_2$O (2:1 by volume), and then stirred at about 80° C. for about 5 hours. After the reaction solution was cooled to room temperature, 40 mL of water was added to the reaction solution, which was then extracted three times with 50 mL of diethylether. The organic phase was collected and was dried using magnesium sulfate to evaporate the solvent. The residue was separated and purified using silica gel column chromatography to obtain 2.61 g of Intermediate I-4 (yield 76%). This compound was identified using LC-MS. C$_{26}$H$_{17}$N; M$^+$343.1

Synthesis of Compound 24

1.71 g (5.0 mmol) of Intermediate I-4, 2.38 g (5.0 mmol) of Intermediate I-5, 0.1 g (0.5 mmol) of 1,10-phenanthroline, 0.19 g (1.0 mmol) of CuI, and 2.07 g (15.0 mmol) of K$_2$CO$_3$ were dissolved in 20 mL of DMF, and then stirred at about 80° C. for about 24 hours. The reaction solution was cooled to room temperature, and then extracted three times with 20 mL or water and 20 mL of diethylether. The organic phase was collected and was dried using magnesium sulfate to evaporate the solvent. The residue was separated and purified using silica gel column chromatography to obtain 2.69 g of Compound 24 (yield: 72%). This compound was identified using mass spectroscopy/fast atom bombardment (MS/FAB) and $^1$H NMR. C$_{56}$H$_{38}$N$_2$ cal. 738.30. found 739.32

$^1$H NMR (CDCl$_3$, 400 MHz) • • 8.14-8.11 (m, 4H), 7.65-7.60 (m, 6H), 7.53-7.34 (m, 18H), 7.17-7.13 (m, 2H), 7.07 (s, 2H), 7.01-6.92 (m, 6H)

Synthesis Example 3;
Synthesis of Compound 30
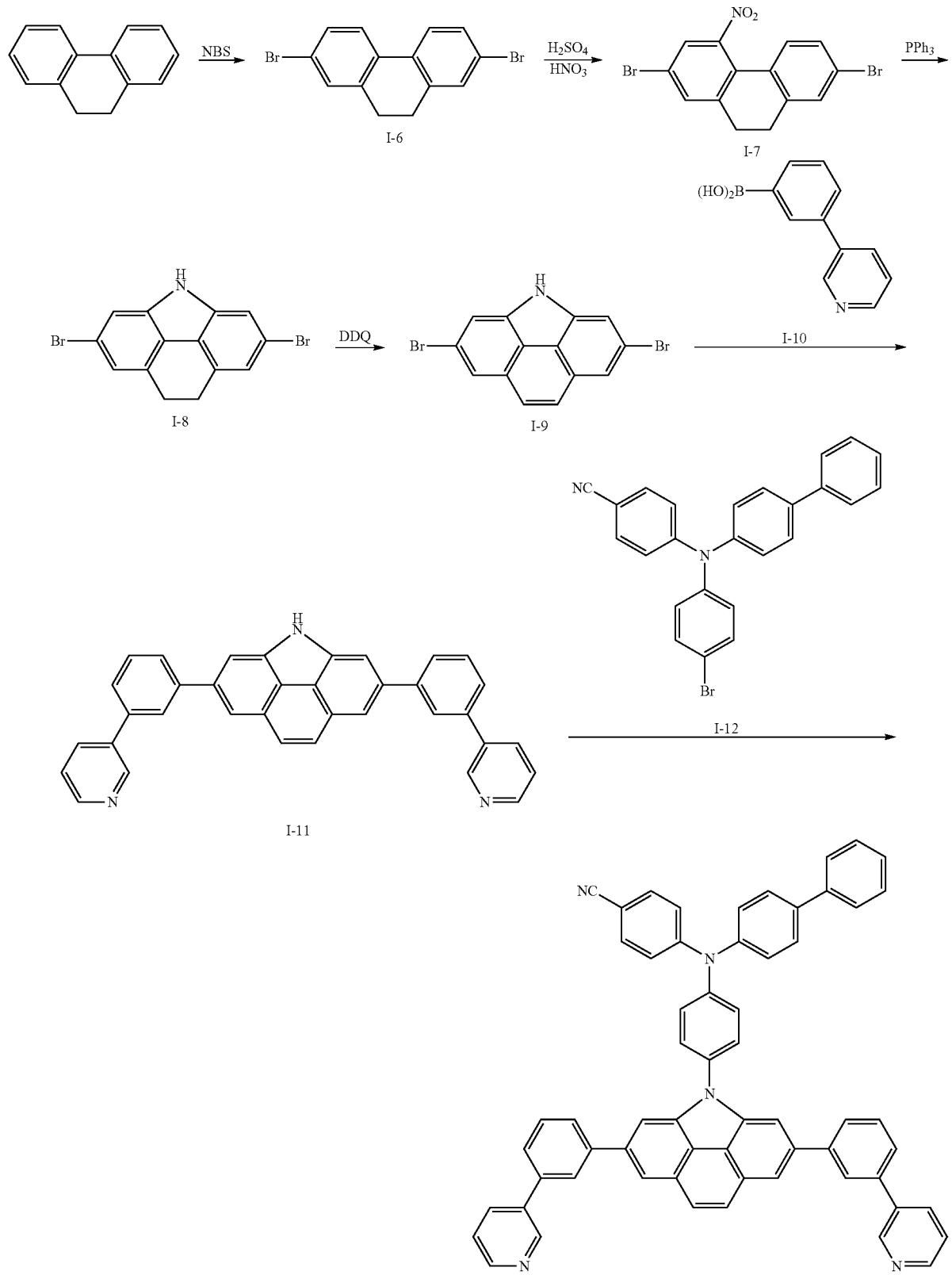

Synthesis of Intermediate I-6

10.0 g (55.4 mmol) of 9,10-dihydrophenanthrene, 21.8 g (121.0 mmol) of N-bromosuccinimide, and 0.51 g (2.7 mmol) of p-TsOH were dissolved in 30 mL of acetonitril, and then stirred at about 50° C. for about 12 hours. The reaction solution was cooled to room temperature, and then stirred for about 30 minutes to precipitate crystals. The crystals were collected using a filter under reduced pressure, and then washed with methanol to 8.42 g of Intermediate 1-6 as gray crystals (yield: 45%). This compound was identified using LC-MS. $C_{14}H_{10}Br_2$ $M^+335.9$

Synthesis of Intermediate I-7

5.07 g (15.0 mmol) of Intermediate I-6 was completely dissolved in 50 mL of dichloromethane, followed by an addition of 1.89 g (30.0 mmol) of nitric acid at room temperature to obtain a mixture. 1.47 g (15.0 mmol) of sulfuric acid was slowly dropwise added to the mixture and then stirred at about 30° C. for about 6 hours. After completion of the reaction, the reaction solution was cooled to room temperature. Then, 50 mL of methanol was added thereto and stirred for about 2 hours to precipitate crystals. The crystals were collected using a filter under reduced pressure, and then washed with methanol to obtain 5.21 g of Intermediate I-7 as yellow crystals (yield: 90%). This compound was identified using LC-MS. $C_{14}H_9Br_2NO_2$ $M^+380.9$

Synthesis of Intermediate I-8

4.59 g (12.0 mmol) of Intermediate I-7 was dissolved in 30 mL of o-dichlorobenzene, and heated until it was completely dissolved, followed by an addition of 4.72 g (18.0 mmol) of triphenylphosphine, and stirring at about 180° C. for about 3 hours. The reaction solution was cooled to room temperature, and the solvent was evaporated from the solution. The residue was separated and purified using silica gel column chromatography, and washed with methanol to obtain 2.91 g of Intermediate I-8 as white crystals (yield: 70%). This compound was identified using LC-MS. $C_{14}H_{11}Br_2N$ $M^+350.9$

Synthesis of Intermediate I-9

3.53 g (10.0 mmol) of Intermediate I-8 was dissolved in 50 ml of toluene in an oxygen atmosphere, followed by an addition of 0.68 g (3.0 mmol) of 2,3-dichloro-5,6-dicyano-1,4-benzoquinone, and 0.21 g (3.0 mmol) of $NaNO_2$ thereto at room temperature to obtain a mixture, which was then stirred at about 110° C. for about 6 hours. After completion of the reaction, the reaction solution was cooled to room temperature. The solvent was evaporated from the solution. The residue was separated and purified using silica gel column chromatography to obtain 3.14 g of Intermediate I-9 (yield: 90%). This compound was identified using LC-MS. $C_{14}H_7Br_2N$ $M^+346.8$

Synthesis of Intermediate I-11

2.78 g of Intermediate I-11 (yield: 56%) was obtained using Intermediate I-9 and Intermediate I-10 in the same manner as in the synthesis of Intermedate I-4. This compound was identified using LC-MS. $C_{36}H_{23}N_3$ $M^+497.2$

Synthesis of Compound 30

2.61 g of Compound 30 (yield: 62%) was obtained using Intermediate I-11 and Intermediate I-12 in the same manner as in the synthesis of Compound 24. This compound was identified using MS/FAB and $^1H$ NMR. $C_{61}H_{39}N_5$ cal. 841.32. found 842.35

$^1H$ NMR (CDCl$_3$, 400 MHz) • • 8.91 (s, 2H), 8.65 (d, 2H), 8.16 (s, 2H), 7.98 (s, 2H), 7.92 (dd, 2H), 7.70-7.62 (m, 4H), 7.59 (s, 2H), 7.53-7.25 (m, 15H), 7.12-7.08 (m, 2H), 6.96-6.89 (m, 6H)

Additional compounds were synthesized using appropriate intermediate materials according to the synthetic pathways and the methods described as above, and were identified using $^1H$ NMR and MS/FAB. The results are shown in Table 1 below.

Synthetic pathways and source materials for other compounds not in Table 1 will be obvious to one of ordinary skill in the art based on the synthetic pathways and source materials described above.

TABLE 1

| Compound | $^1H$ NMR (CDCl$_3$, 400 MHz) | MS/FAB found | calc. |
|---|---|---|---|
| 2 | 7.77 (d, 2H), 7.65-7.61 (m, 4H), 7.54-7.38 (m, 16H), 7.15-7.11 (m, 2H), 7.05-6.98 (m, 6H) | 587.36 | 586.24 |
| 3 | 7.78-7.76 (m, 3H), 7.65-7.61 (m, 2H), 7.56-7.39 (m, 12H), 7.35-7.32 (m, 1H), 7.24-7.20 (m, 2H), 7.14-7.10 (m, 2H), 7.08-7.04 (m, 2H), 7.02-6.98 (m, 1H), 6.83-6.79 (m, 2H), 6.72 (d, 1H), 1.65 (s, 6H) | 627.31 | 626.27 |
| 8 | 7.77 (d, 2H), 7.65-7.61 (m, 2H), 7.54 (s, 2H), 7.53-7.48 (m, 4H), 7.46-7.35 (m, 7H), 7.18-7.14 (m, 2H), 7.06-7.01 (m, 6H) | 536.22 | 535.20 |
| 13 | 7.78 (d, 2H), 7.69-7.64 (m, 4H), 7.56-7.40 (m, 13H), 7.21-7.13 (m, 4H), 7.07 (s, 2H), 7.01-6.97 (m, 2H), 6.96-6.93 (m, 1H), 6.83-6.79 (m, 2H) | 587.23 | 586.24 |
| 17 | 8.21 (d, 1H), 7.78 (d, 2H), 7.66-7.64 (m, 2H), 7.56-7.35 (m, 17H), 7.34-7.23 (m, 4H), 7.18-7.14 (m, 2H), 7.06-7.02 (m, 2H), 9.94-6.91 (m, 3H) | 676.29 | 675.27 |
| 20 | 8.11 (s, 1H), 8.06 (s, 1H), 7.77-7.72 (m, 2H), 7.68-7.38 (m, 15H), 7.26 (d, 1H), 7.21 (dd, 1H), 7.16-7.07 | 612.27 | 611.24 |

TABLE 1-continued

| Compound | ¹H NMR (CDCl₃, 400 MHz) | MS/FAB found | MS/FAB calc. |
|---|---|---|---|
| | (m, 3H), 6.99-6.96 (m, 2H), 6.85-6.83 (m, 2H), 6.81 (d, 1H) | | |
| 23 | 8.45 (s, 2H), 8.07 (d, 2H), 7.67 (d, 2H), 7.64 (d, 2H), 7.52-7.34 (m, 5H), 7.23-7.20 (m, 4H), 7.13-7.09 (m, 4H), 6.99 (dd, 1H), 6.82 (d, 2H) | 561.23 | 560.20 |
| 24 | 8.14-8.11 (m, 4H), 7.65-7.60 (m, 6H), 7.53-7.34 (m, 18H), 7.17-7.13 (m, 2H), 7.07 (s, 2H), 7.01-6.92 (m, 6H) | 739.32 | 738.30 |
| 30 | 8.91 (s, 2H), 8.65 (d, 2H), 8.16 (s, 2H), 7.98 (s, 2H), 7.92 (dd, 2H), 7.70-7.62 (m, 4H), 7.59 (s, 2H), 7.53-7.25 (m, 15H), 7.12-7.08 (m, 2H), 6.96-6.89 (m, 6H) | 842.35 | 841.32 |
| 33 | 8.17 (d, 1H), 7.87 (d, 1H), 7.78 (d, 2H), 7.54 (s, 2H), 7.51-7.36 (m, 15H), 7.23 (dd, 1H), 7.18-7.14 (m, 2H), 7.05 (d, 1H), 6.95-6.92 (m, 2H) | 586.23 | 585.22 |
| 35 | 7.78 (d, 2H), 7.65-7.61 (m, 4H), 7.54-7.34 (m, 22H), 7.16-7.12 (m, 4H), 6.99-6.95 (m, 2H) | 663.28 | 662.27 |
| 36 | 7.79-7.76 (m, 3H), 7.64-7.61 (m, 2H), 7.56-7.30 (m, 19H), 7.25-7.19 (m, 2H), 7.06 (d, 1H), 6.98-6.94 (m, 4H), 6.83 (d, 1H), 1.65 (s, 6H) | 703.31 | 702.30 |
| 37 | 7.87 (d, 1H), 7.77 (d, 2H), 7.64-7.62 (m, 2H), 7.57 (d, 1H), 7.54-7.34 (m, 18H), 7.26-7.13 (m, 11H), 7.11 (d, 1H), 7.07 (d, 1H), 6.97-6.93 (m, 4H), 6.84 (d, 1H) | 827.35 | 826.33 |
| 38 | 7.92 (d, 2H), 7.88 (d, 1H), 7.78 (d, 2H), 7.66-7.59 (m, 3H), 7.56-7.32 (m, 20H), 7.25-7.18 (m, 3H), 7.06 (d, 1H), 6.99-6.96 (m, 3H), 6.93-6.89 (m, 4H), 6.83 (d, 1H) | 825.33 | 824.32 |
| 41 | 9.01 (s, 1H), 8.70 (d, 1H), 8.16 (d, 1H), 7.92 (d, 1H), 7.87 (d, 1H), 7.76 (d, 2H), 7.54 (s, 2H), 7.51-7.21 (m, 17H), 7.11-7.06 (m, 4H), 6.96 (d, 1H) | 638.26 | 637.25 |
| 42 | 8.12 (d, 4H), 7.65-7.61 (m, 6H), 7.53-7.34 (m, 24H), 7.09 (s, 2H), 7.01-6.98 (d, 4H), 6.96-6.93 (d, 2H) | 815.35 | 814.33 |
| 49 | 8.10 (s, 1H), 7.89 (d, 2H), 7.78 (d, 2H), 7.74 (d, 1H), 7.64 (d, 4H), 7.54-7.38 (m, 18H), 7.11 (d, 1H), 7.01-6.98 (d, 4H) | 664.29 | 663.27 |
| 51 | 7.77 (d, 2H), 7.68 (d, 1H), 7.64-7.61 (m, 5H), 7.56-7.36 (m, 17H), 7.30 (d, 1H), 7.09 (d, 1H), 7.03-6.98 (m, 5H), 1.61 (s, 6H) | 703.33 | 702.30 |
| 52 | 7.78 (d, 2H), 7.66 (d, 1H), 7.64-7.61 (m, 4H) 7.55-7.35 (m, 16H), 7.31-7.7.24 (m, 5H), 7.15-7.08 (m, 7H), 7.05 (d, 1H), 6.99-6.66 (m, 5H), 6.83 (s, 1H) | 827.35 | 826.33 |
| 53 | 8.09 (d, 1H), 7.85 (s, 1H), 7.82 (d, 1H), 7.78 (d, 2H), 7.66-7.63 (d, 4H), 7.55-7.38 (m, 16H), 7.32 (d, 1H), 7.11 (d, 1H), 7.05 (s, 1H), 7.02-6.99 (d, 4H) | 677.26 | 676.25 |
| 56 | 8.31-8.27 (m, 2H), 7.78-7.75 (m, 3H), 7.70 (s, 1H), 7.68 (s, 1H), 7.64-7.62 (m, 3H), 7.58 (d, 1H), 7.52-7.30 (m, 14H), 7.26-7.23 (m, 2H), 7.15 (d, 1H), 7.03 (d, 1H), 7.04-6.98 (m, 3H), 1.64 (s, 6H) | 727.32 | 726.30 |
| 57 | 7.79-7.76 (m, 4H), 7.73 (d, 2H), 7.66 (d, 2H), 7.55-7.41 (m, 14H), 7.36 (d, 2H), 7.21 (d, 2H), 7.09 (s, 2H), 7.03-6.99 (m, 2H) | 691.24 | 690.23 |

Example 1

To manufacture an anode, a corning 15 Ω/cm2 (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

4,4',4"-Tris(N-(2-naphthyl)-N-phenyl-amino)-triphenylamine (hereinafter, 2-TNATA), was vacuum-deposited on the anode to a thickness of 600 Å to form an HIL, and Compound 3 as a hole transporting compound was vacuum-deposited on the HIL to a thickness of 300 Å to form a HTL.

9,10-Di-naphthalene-2-yl-anthracene (hereinafter, DNA) as a known blue fluorescent host, and 4,4'-bis[2-(4-(N,N-diphenylamino)phenyl)vinyl]biphenyl (hereinafter, DPAVBi) as a known blue fluorescent dopant, were co-deposited in a weight ratio of about 98:2 on the HTL to form an EML having a thickness of about 300 Å.

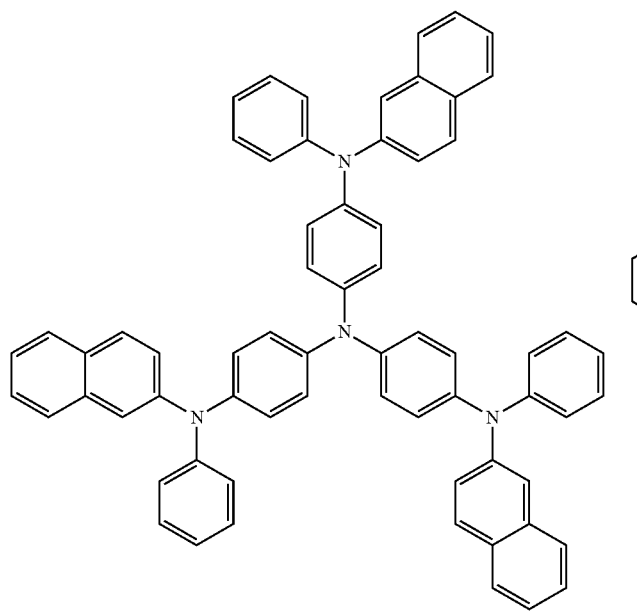

2-THATA

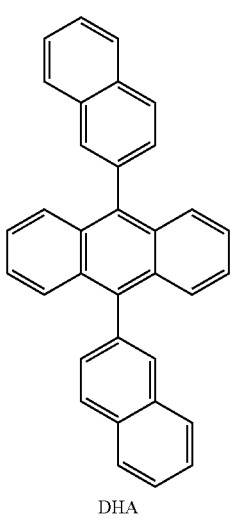

DHA

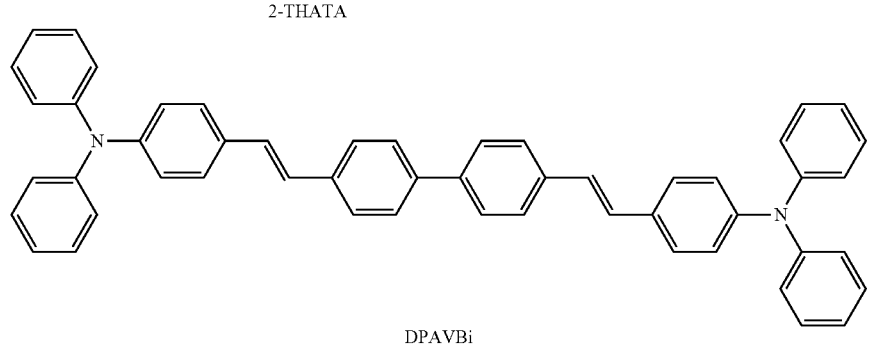

DPAVBi

Then, Alq₃ was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3000 Å, thereby forming an LiF/Al electrode and completing the manufacture of an organic light-emitting device.

The organic light-emitting device had a driving voltage of about 5.66 V at a current density of 50 mA/cm$^2$, a luminosity of 2,580 cd/m$^2$, a luminescent efficiency of 5.16 cd/A, and a half life-span (hr@100 mA/cm$^2$) of about 218 hours.

Example 2

An organic light-emitting device was manufactured in the same manner as in Example 1, except that Compound 24 was used, instead of Compound 3, to form the HTL.

The organic light-emitting device had a driving voltage of about 5.54 V at a current density of 50 mA/cm$^2$, a luminosity of 2,630 cd/m$^2$, a luminescent efficiency of 5.26 cd/A, and a half life-span (hr@100 mA/cm$^2$) of about 226 hours.

Example 3

An organic light-emitting device was manufactured in the same manner as in Example 1, except that Compound 35 was used, instead of Compound 3, to form the HTL.

The organic light-emitting device had a driving voltage of about 5.52 V at a current density of 50 mA/cm$^2$, a luminosity of 2,655 cd/m$^2$, a luminescent efficiency of 5.31 cd/A, and a half life-span (hr@100 mA/cm$^2$) of about 267 hours.

Example 4

An organic light-emitting device was manufactured in the same manner as in Example 1, except that Compound 37 was used, instead of Compound 3, to form the HTL.

The organic light-emitting device had a driving voltage of about 5.57 V at a current density of 50 mA/cm$^2$, a luminosity of 2,640 cd/m$^2$, a luminescent efficiency of 5.28 cd/A, and a half life-span (hr@100 mA/cm$^2$) of about 235 hours.

Example 5

An organic light-emitting device was manufactured in the same manner as in Example 1, except that Compound 41 was used, instead of Compound 3, to form the HTL.

The organic light-emitting device had a driving voltage of about 5.67 V at a current density of 50 mA/cm$^2$, a luminosity of 2,635 cd/m$^2$, a luminescent efficiency of 5.27 cd/A, and a half life-span (hr@100 mA/cm$^2$) of about 241 hours.

Example 6

An organic light-emitting device was manufactured in the same manner as in Example 1, except that Compound 49 was used, instead of Compound 3, to form the HTL.

The organic light-emitting device had a driving voltage of about 5.78 V at a current density of 50 mA/cm$^2$, a luminosity of 2,565 cd/m$^2$, a luminescent efficiency of 5.13 cd/A, and a half life-span (hr@100 mA/cm$^2$) of about 224 hours.

Example 7

An organic light-emitting device was manufactured in the same manner as in Example 1, except that Compound 53 was used, instead of Compound 3, to form the HTL.

The organic light-emitting device had a driving voltage of about 5.49 V at a current density of 50 mA/cm$^2$, a luminosity of 2,670 cd/m$^2$, a luminescent efficiency of 5.34 cd/A, and a half life-span (hr@100 mA/cm$^2$) of about 226 hours.

Example 8

An organic light-emitting device was manufactured in the same manner as in Example 1, except that Compound 57 was used, instead of Compound 3, to form the HTL.

The organic light-emitting device had a driving voltage of about 5.48 V at a current density of 50 mA/cm$^2$, a luminosity of 2,625 cd/m$^2$, a luminescent efficiency of 5.25 cd/A, and a half life-span (hr@100 mA/cm$^2$) of about 243 hours.

Example 9

2-TNATA was vacuum-deposited on the anode to from a hole injection layer having a thickness of 550 Å, and then 4,4'-bis[N-(1-naphthyl)-N-phenylamino]biphenyl (hereinafter, NPB), which is a known compound for a hole transport layer, was vacuum-deposited on the hole injection layer at a thickness of 250 Å, followed by vacuum-depositing Compound 35 at a thickness of 100 Å as a second hole transport layer. Then, the emission layer is formed in the same manner as in Example 1 to manufacture an organic light-emitting device.

The organic light-emitting device had a driving voltage of about 5.20 V at a current density of 50 mA/cm$^2$, a luminosity of 3,120 cd/m$^2$, a luminescent efficiency of 6.24 cd/A, and a half life-span (hr@100 mA/cm$^2$) of about 367 hours.

Example 10

An organic light-emitting device was manufactured in the same manner as in Example 9, except that Compound 37 was used, instead of Compound 35, as the second hole transport layer.

The organic light-emitting device had a driving voltage of about 5.21 V at a current density of 50 mA/cm$^2$, a luminosity of 3,105 cd/m$^2$, a luminescent efficiency of 6.21 cd/A, and a half life-span (hr@100 mA/cd) of about 351 hours.

Example 11

An organic light-emitting device was manufactured in the same manner as in Example 9, except that Compound 41 was used, instead of Compound 35, as the second hole transport layer.

The organic light-emitting device had a driving voltage of about 5.26 V at a current density of 50 mA/cm$^2$, a luminosity of 3,070 cd/m$^2$, a luminescent efficiency of 6.14 cd/A, and a half life-span (hr@100 mA/cm$^2$) of about 316 hours.

Example 12

An organic light-emitting device was manufactured in the same manner as in Example 9, except that Compound 57 was used, instead of Compound 35, as the second hole transport layer.

The organic light-emitting device had a driving voltage of about 5.17 V at a current density of 50 mA/cm$^2$, a luminosity of 3,155 cd/m$^2$, a luminescent efficiency of 6.31 cd/A, and a half life-span (hr@100 mA/cm$^2$) of about 337 hours.

Comparative Example 1

An organic light-emitting device was manufactured in the same manner as in Example 1, except that a known compound NPB was used, instead of Compound 3, to form the HTL.

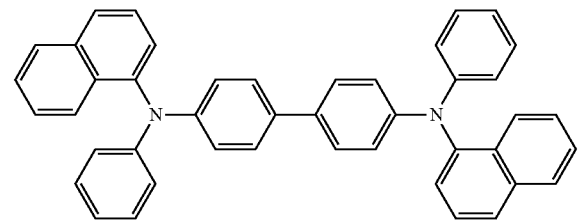

NPB

The organic light-emitting device had a driving voltage of about 7.35 V at a current density of 50 mA/cm$^2$, a luminosity of 2,065 cd/m$^2$, a luminescent efficiency of 4.13 cd/A, and a half life-span (hr@100 mA/cm$^2$) of about 145 hours.

The organic light-emitting devices manufactured using the compounds represented by Formula 1 according to embodiments as HTL materials had significantly lower driving voltages and improved I-V-L characteristics. In particular, the organic light-emitting devices according to the embodiments had markedly improved lifetimes. Particularly, in Examples 9 to 12 when the compound of Formula 1 was used as the second hole transport layer, a luminescent efficiency was significantly increased, and a life-span was remarkably improved. The characteristics of the organic light-emitting devices of Examples 1-12 and Comparative Example 1 are shown in Table 2 below.

TABLE 2

| | HTL material | Driving voltage (V) | Current density (mA/cm²) | Luminance (cd/m²) | Efficiency (cd/A) | Emission color | Half-life span (hr @ 100 mA/cm²) |
|---|---|---|---|---|---|---|---|
| Example 1 | Compound 3 | 5.66 | 50 | 2,580 | 5.16 | Blue | 218 hr |
| Example 2 | Compound 24 | 5.54 | 50 | 2,630 | 5.26 | Blue | 226 hr |
| Example 3 | Compound 35 | 5.52 | 50 | 2,655 | 5.31 | Blue | 267 hr |
| Example 4 | Compound 37 | 5.57 | 50 | 2,640 | 5.28 | Blue | 235 hr |
| Example 5 | Compound 41 | 5.67 | 50 | 2,635 | 5.27 | Blue | 241 hr |
| Example 6 | Compound 49 | 5.78 | 50 | 2,565 | 5.13 | Blue | 224 hr |
| Example 7 | Compound 53 | 5.49 | 50 | 2,670 | 5.34 | Blue | 226 hr |
| Example 8 | Compound 57 | 5.48 | 50 | 2,625 | 5.25 | Blue | 243 hr |
| Example 9 | Compound 35 | 5.20 | 50 | 3,120 | 6.24 | Blue | 367 hr |
| Example 10 | Compound 37 | 5.21 | 50 | 3,105 | 6.21 | Blue | 351 hr |
| Example 11 | Compound 41 | 5.26 | 50 | 3,070 | 6.14 | Blue | 316 hr |
| Example 12 | Compound 57 | 5.17 | 50 | 3,155 | 6.31 | Blue | 337 hr |
| Comparative Example 1 | 2-TNATA | 7.35 | 50 | 2,065 | 4.13 | Blue | 145 hr |

The novel heterocyclic compound represented by Formula 1 above has an excellent charge transporting capability, and so, can be used as a hole injecting material or a hole transporting material that is suitable for any color fluorescent and phosphorescent devices, such as red, green, blue, and white fluorescent and phosphorescent devices. In particular, the compound of Formula 1 includes a heterocyclic compound in the molecule and thus has a high T1 energy level, characteristics of a high LUMO energy level, and characteristics of a HOMO energy level that is similar or a little deeper compared to NPB, which is a conventional hole transport material. Due to such characteristics, when the compound of Formula 1 is used as a hole injection layer material, electrons being injected from an emission layler to a hole transport layer may be suppressed, and particularly, excitons that are generated in the emission layer may be effectively prevented from being diffused into the hole transport layer. Particularly, among the compounds of Formula 1, when a material with a HOMO energy level that is a little deeper than a conventional hole transport layer is used as a second hole transport layer, such effect are further increased, and thus a luminescent efficiency of the device may be increased, and a life-span of the device may be increased. Therefore, organic light-emitting devices having high efficiency, low driving voltages, high luminance, and long lifetime may be manufactured using the compounds.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A compound represented by Formula 1 below:

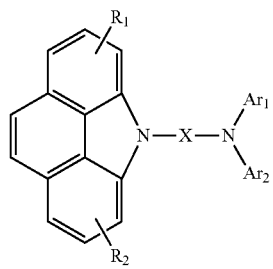

<Formula 1> wherein, in Formula 1, $R_1$ and $R_2$ are each independently a hydrogen atom, a deuterium atom, a halogen atom, a cyano group, a nitro group, a C1-C60 alkylsilyl group, a C1-C60 arylsilyl group, a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C6-C60 aryl group, a substituted or unsubstituted C3-C60 heteroaryl group, a substituted or unsubstituted C6-C60 aryloxy group, or a substituted or unsubstituted C6-C60 arylthio group; X is a substituted or unsubstituted C6-C60 arylene group, a substituted or unsubstituted C3-C60 heteroarylene group, or a substituted or unsubstituted C6-C60 condensed polycyclic group; and $Ar_1$ and $Ar_2$ are each independently a substituted or unsubstituted C6-C60 aryl group, a substituted or unsubstituted C3-C60 heteroaryl group, or a substituted or unsubstituted C6-C60 condensed polycyclic group.

2. The compound of claim 1, wherein, in Formula 1, $Ar_1$ and $Ar_2$ are linked to form a ring.

3. The compound of claim 1, wherein, in Formula 1, $R_1$ and $R_2$ are each independently, one of the groups represented by a hydrogen atom, a deuterium atom, CN, F, $CF_3$, $Si(R_{40})_3$, or

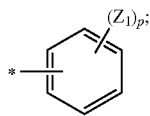

$Z_1$ is a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen group, a cyano group, a nitro group, a hydroxy group, or a carboxy group; $R_{40}$ is a substituted or unsubstituted C1-C20 alkyl group, a substituted or unsubstituted C5-C20 aryl group, a substituted or unsubstituted C3-C20 heteroaryl group, or a substituted or unsubstituted C6-C20 condensed polycyclic group; p is an integer from 1 to 5; and * represents a binding site.

4. The compound of claim 1, wherein, in Formula 1, X is one of the groups represented by Formulae 2a to 2g:

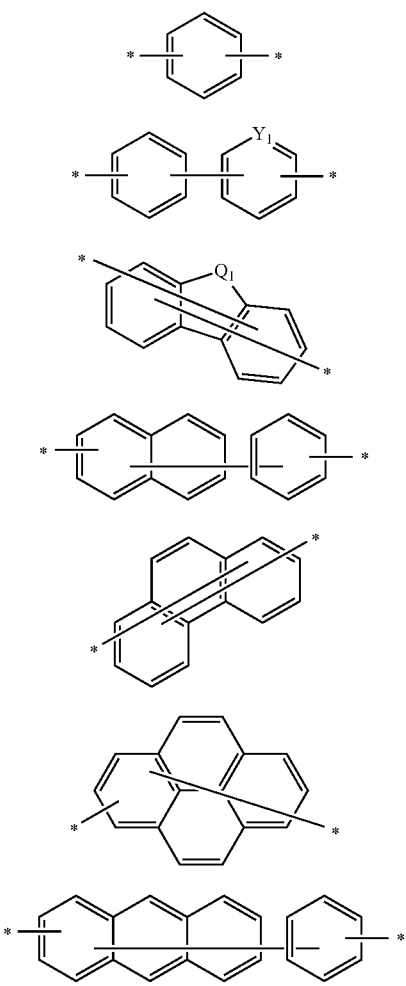

wherein, in Formulae 2a to 2g, $Q_1$ is represented by $-C(R_{30})(R_{31})-$, $-S-$, $-O-$, or $-NR_{32}-$; $Y_1$ is CH or N; $R_{30}$, $R_{31}$, and $R_3$ are each independently, a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen group, a cyano group, a nitro group, a hydroxy group, or a carboxy group; and * represents a binding site.

5. The compound of claim 1, wherein, in Formula 1, $Ar_1$ and $Ar_2$ are each independently one of the groups represented by Formulae 3a to 3e below:

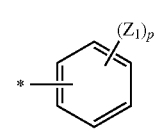

3a

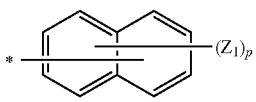

3b

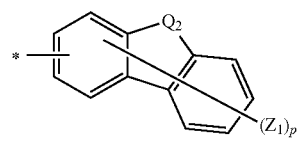

3c

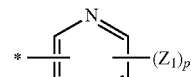

3d

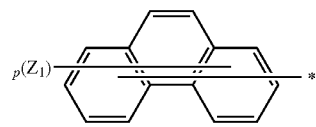

3e wherein, in Formulae 3a to 3e, $Q_2$ is represented by $-C(R_{30})(R_{31})-$, $-N(R_{32})-$, $-S-$, or $-O-$; $Z_1$, $R_{30}$, $R_{31}$, and $R_{32}$ are each independently, a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, $-Si(R_{40})_3$, a halogen group, a cyano group, a nitro group, a hydroxy group or a carboxy group; $R_{40}$ is a substituted or unsubstituted C1-C20 alkyl group, a substituted or unsubstituted C5-C20 aryl group, a substituted or unsubstituted C3-C20 heteroaryl group, or a substituted or unsubstituted C6-C20 condensed polycyclic group; p is an integer from 1 to 9; and * represents a binding site.

6. The compound of claim 1, wherein the compound of Formula 1 is one of the following compounds:
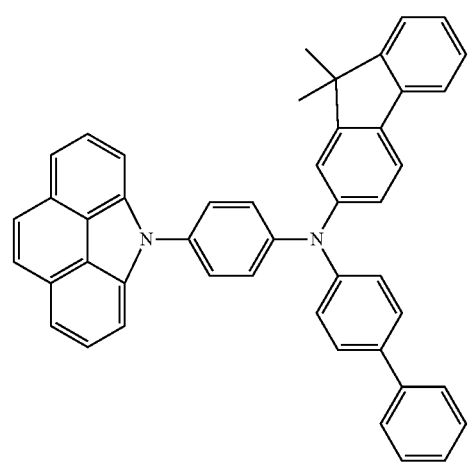
3
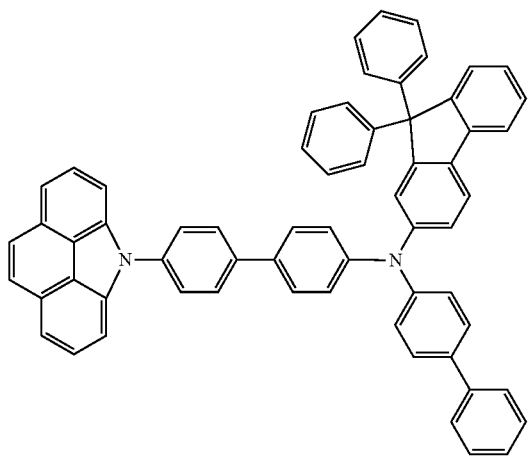
37
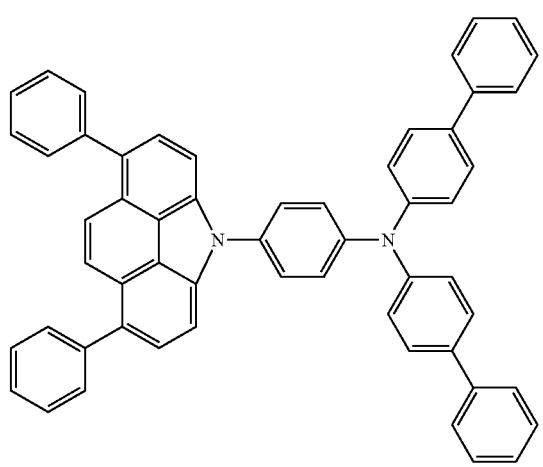
24
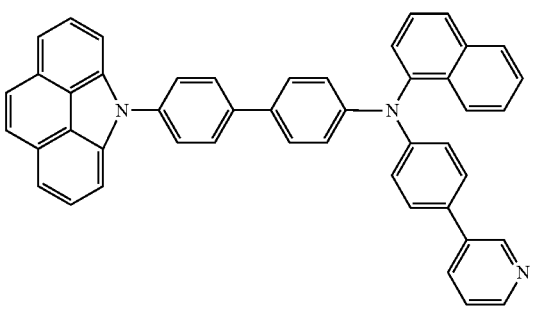
41
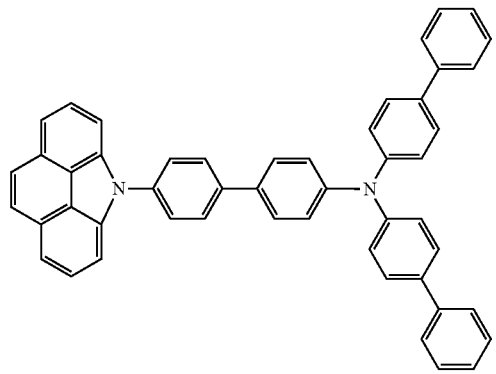
35
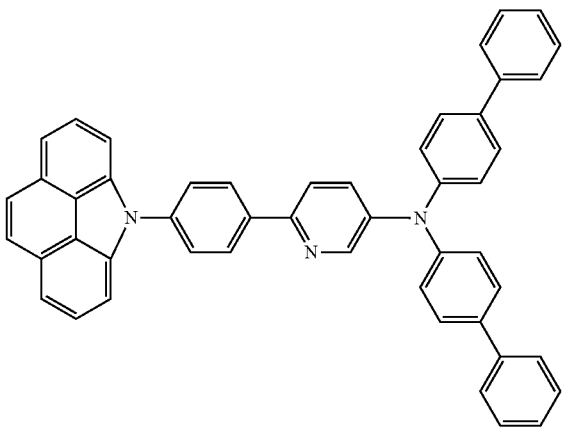
49

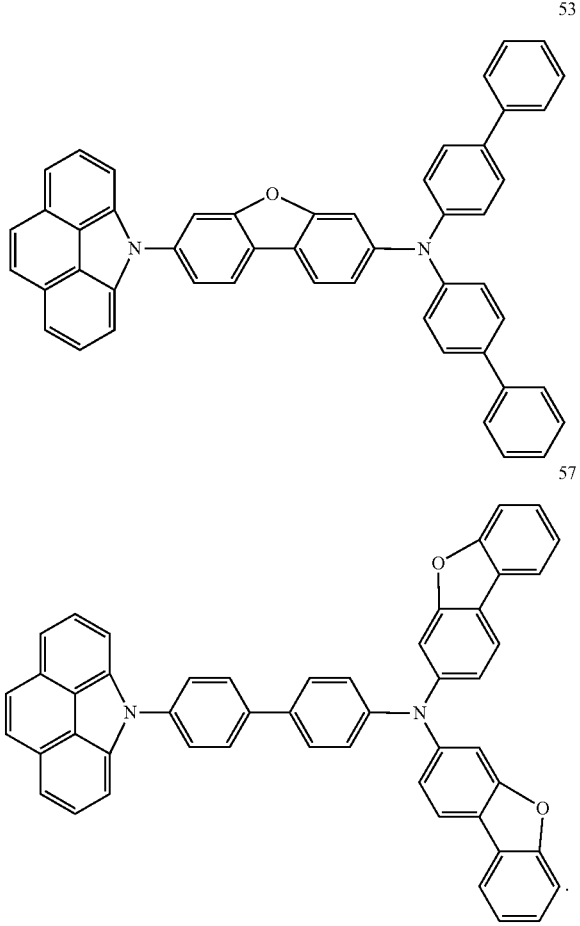

7. An organic light-emitting device comprising:
a first electrode;
a second electrode; and
an organic layer disposed between the first electrode and the second electrode, wherein the organic layer comprises a compound of claim 1.

8. The organic light-emitting device of claim 7, wherein the organic layer is a hole injection layer, a hole transport layer, or a functional layer having both hole injection and hole transport capabilities, wherein the hole transport layer or the functional layer having both hole injection and hole transport capabilities comprises more than one layer.

9. The organic light-emitting device of claim 7, wherein the organic light-emitting device comprises an emission layer, an electron injection layer, an electron transport layer, a functional layer having both electron injection and transport capabilities; a hole injection layer, a hole transport layer, or a functional layer having both hole injection and transport capabilities, wherein at least one of the hole injection layer, the hole transport layer, or the functional layer having both hole injection and hole transport capabilities comprises a compound of claim 1; and wherein the emission layer comprises an anthracene-based compound, an arylamine-based compound, or a styryl-based compound.

10. The organic light-emitting device of claim 7, wherein the organic light-emitting device comprises an emission layer, an electron injection layer, an electron transport layer, a functional layer having both electron injection and transport capabilities, a hole injection layer, a hole transport layer, or a functional layer having both hole injection and transport capabilities; wherein at least one of the hole injection layer, the hole transport layer, and the functional layer having both hole injection and hole transport capabilities comprises the compound of claim 1; and wherein the emission layer comprises red, green, blue, and white emission layers one or more of which comprises a phosphorescent compound.

11. The organic light-emitting device of claim 10, wherein the hole injection layer, the hole transport layer, or the functional layer having both hole injection or hole transport capabilities comprises a charge-generating material.

12. The organic light-emitting device of claim 11, wherein the charge-generating material is a p-dopant.

13. The organic light-emitting device of claim 12, wherein the p-dopant is a quinon derivative.

14. The organic light-emitting device of claim 12, wherein the p-dopant is a metal oxide.

15. The organic light-emitting device of claim 12, wherein the p-dopant is a cyano group-containing compound.

16. The organic light-emitting device of claim 7, wherein the organic layer comprises an electron transport layer, and wherein the electron transport layer further comprises a metal complex.

17. The organic light-emitting device of claim 16, wherein the metal complex is a lithium complex.

18. The organic light-emitting device of claim 16, wherein the metal complex is a lithium quinolate (LiQ).

19. The organic light-emitting device of claim 7, wherein the organic layer is formed from the compound of claim 1 using a wet process.

20. A flat panel display device comprising the organic light-emitting device of claim 7, wherein the first electrode of the organic light-emitting device is electrically connected to a source electrode or a drain electrode of a thin-film transistor.

* * * * *